United States Patent
Yamaguchi et al.

(10) Patent No.: US 9,233,519 B2
(45) Date of Patent: Jan. 12, 2016

(54) WATER-ABSORBENT SHEET STRUCTURE

(75) Inventors: Kiyoshi Yamaguchi, Himeji (JP); Syuji Tsuno, Kako-gun (JP); Haruka Inaba, Himeji (JP); Masayoshi Handa, Himeji (JP)

(73) Assignee: SUMITOMO SEIKA CHEMICALS CO., LTD., Kako-gun (JP)

( * ) Notice: Subject to any disclaimer, the term of this patent is extended or adjusted under 35 U.S.C. 154(b) by 761 days.

(21) Appl. No.: 13/521,376

(22) PCT Filed: Dec. 27, 2010

(86) PCT No.: PCT/JP2010/073538
§ 371 (c)(1),
(2), (4) Date: Jul. 10, 2012

(87) PCT Pub. No.: WO2011/086844
PCT Pub. Date: Jul. 21, 2011

(65) Prior Publication Data
US 2012/0308799 A1 Dec. 6, 2012

(30) Foreign Application Priority Data
Jan. 13, 2010 (JP) .................. 2010-004936

(51) Int. Cl.
*B32B 5/26* (2006.01)
*A61F 13/49* (2006.01)
(Continued)

(52) U.S. Cl.
CPC ................. *B32B 5/26* (2013.01); *A61F 13/534* (2013.01); *A61F 13/49* (2013.01);
(Continued)

(58) Field of Classification Search
CPC ......... A61F 13/49; A61F 13/15; A61L 15/60; Y10T 428/2982
USPC ................................. 428/220, 341
See application file for complete search history.

(56) References Cited

U.S. PATENT DOCUMENTS 5,562,646 A 10/1996 Goldman et al.
(Continued)

FOREIGN PATENT DOCUMENTS

CN 101495543 A 7/2009
EP 0 948 952 A1 10/1999
(Continued)

OTHER PUBLICATIONS

Office Action issued Oct. 14, 2014 in Taiwanese Patent Application No. 100101120.
(Continued)

*Primary Examiner* — Aaron Austin
*Assistant Examiner* — Michael Zhang
(74) *Attorney, Agent, or Firm* — Oblon, McClelland, Maier & Neustadt, L.L.P.

(57) ABSTRACT

A water-absorbent sheet structure comprises a structure in which an absorbent layer containing a water-absorbent resin (A) and a water-absorbent resin (B) is sandwiched with fibrous webs from an upper side and a lower side of the absorbent layer, characterized in that the water-absorbent resin (A) and the water-absorbent resin (B) are contained in a total amount of from 100 to 1,000 g/m², and that the water-absorbent resin (A) and the water-absorbent resin (B) have the following properties: (1) the water-absorbent resin (A) having a water-retention capacity of saline solution (Ra) from 15 to 55 g/g; (2) the water-absorbent resin (B) having a water-retention capacity of saline solution (Rb) from 10 to 50 g/g; and (3) Ra and Rb mentioned above satisfies the relationship of the following formula: Ra−Rb≥(g/g). The water-absorbent sheet structure of the present invention exhibits some effects that a water-absorbent sheet structure has excellent shape retaining ability even when the structure is thin, so that the water-absorbent sheet structure does not undergo deformation of the form before liquid absorption or after the absorption, and is capable of sufficiently exhibiting absorbent properties.

13 Claims, 4 Drawing Sheets

(51) Int. Cl.
*A61F 13/00* (2006.01)
*A61F 13/534* (2006.01)
*A61F 13/15* (2006.01)
*A61F 13/53* (2006.01)

(52) U.S. Cl.
CPC ............ *A61F 2013/15463* (2013.01); *A61F 2013/5307* (2013.01); *A61F 2013/530481* (2013.01); *A61F 2013/530554* (2013.01); *A61F 2013/530715* (2013.01); *A61F 2013/530737* (2013.01); *B32B 2262/0253* (2013.01); *B32B 2262/0276* (2013.01); *B32B 2262/04* (2013.01); *B32B 2307/726* (2013.01); *Y10T 428/26* (2015.01); *Y10T 428/273* (2015.01); *Y10T 442/659* (2015.04)

(56) References Cited

U.S. PATENT DOCUMENTS

| | | | |
|---|---|---|---|
| 5,599,335 | A | 2/1997 | Goldman et al. |
| 5,669,894 | A | 9/1997 | Goldman et al. |
| 5,760,080 | A | 6/1998 | Wada et al. |
| 5,836,929 | A * | 11/1998 | Bewick-Sonntag A61F 13/15203 604/368 |
| 5,567,744 | A | 10/1996 | Nagata et al. |
| 6,054,541 | A | 4/2000 | Wada et al. |
| 6,180,724 | B1 | 1/2001 | Wada et al. |
| 6,323,387 | B1 | 11/2001 | Soga et al. |
| 6,790,798 | B1 | 9/2004 | Suzuki et al. |
| 2004/0254553 | A1* | 12/2004 | Fujimaru et al. ............ 604/372 |
| 2005/0049379 | A1* | 3/2005 | Adachi et al. ................ 526/319 |
| 2005/0222547 | A1* | 10/2005 | Beruda et al. ............... 604/368 |
| 2006/0173434 | A1* | 8/2006 | Zoromski et al. ........... 604/374 |
| 2007/0027436 | A1 | 2/2007 | Nakagawa et al. |
| 2009/0118432 | A1* | 5/2009 | Fukudome et al. ......... 525/329.9 |
| 2009/0326162 | A1 | 12/2009 | Kobushi et al. |
| 2011/0111199 | A1 | 5/2011 | Takatori et al. |
| 2011/0151228 | A1 | 6/2011 | Takatori et al. |
| 2011/0270204 | A1 | 11/2011 | Fukudome et al. |
| 2011/0276019 | A1 | 11/2011 | Kakimoto et al. |
| 2012/0029456 | A1 | 2/2012 | Takatori et al. |
| 2012/0089108 | A1 | 4/2012 | Ueda et al. |
| 2012/0203191 | A1 | 8/2012 | Maruo et al. |

FOREIGN PATENT DOCUMENTS

| | | | |
|---|---|---|---|
| EP | 2 387 981 | A1 | 11/2011 |
| EP | 2 441 420 | A1 | 4/2012 |
| FR | 2 627 080 | A1 | 8/1989 |
| JP | 2 48944 | | 2/1990 |
| JP | 5-320523 | A | 12/1993 |
| JP | 6 59039 | | 8/1994 |
| JP | 7 51315 | | 2/1995 |
| JP | 8 57311 | | 3/1996 |
| JP | 9 253129 | | 9/1997 |
| JP | 9 510889 | | 11/1997 |
| JP | 2000 238161 | | 9/2000 |
| JP | 2001 96654 | | 4/2001 |
| JP | 2001 158074 | | 6/2001 |
| JP | 2001 252307 | | 9/2001 |
| JP | 2001252307 | A * | 9/2001 |
| JP | 2002 325799 | | 11/2002 |
| JP | 2003 11118 | | 1/2003 |
| JP | 2003-192732 | A | 7/2003 |
| JP | 2005 334616 | | 12/2005 |
| JP | 2007 319170 | | 12/2007 |
| WO | WO 95/26209 | A1 | 10/1995 |

OTHER PUBLICATIONS

U.S. Appl. No. 13/695,515, filed Oct. 31, 2012, Fukudome, et al.
U.S. Appl. No. 13/819,591, filed Feb. 27, 2013, Matsushita, et al.
U.S. Appl. No. 14/369,580, filed Jun. 27, 2014, Matsushita, et al.
International Search Report Issued Mar. 29, 2011 in PCT/JP10/73538 Filed Dec. 27, 2010.
U.S. Appl. No. 13/521,491, filed Jul. 11, 2012, Fukudome, et al.
U.S. Appl. No. 13/521,572, filed Jul. 11, 2012, Matsushita, et al.
U.S. Appl. No. 13/521,464, filed Jul. 11, 2012, Hinayama, et al.
Extended Search Report issued Sep. 20, 2013 in European Patent Application No. 10843197.4.
U.S. Appl. No. 13/637,153, filed Sep. 25, 2012, Takatori, et al.
Office Action issued Jun. 1, 2015 in Japanese Patent Application No. 2011-549907.

* cited by examiner

WATER-ABSORBENT SHEET STRUCTURE

TECHNICAL FIELD

The present invention relates to a water-absorbent sheet structure which can be used in the fields of hygienic materials and the like. More specifically, the present invention relates to a water-absorbent sheet structure which is thin and can be suitably used in absorbent articles, such as disposable diapers. In addition, the present invention relates to an absorbent article such as disposable diapers using the water-absorbent sheet structure.

BACKGROUND ART

Absorbent articles represented by disposable diapers or the like have a structure in which an absorbent material for absorbing a liquid such as a body liquid is sandwiched with a flexible liquid-permeable surface sheet (top sheet) positioned on a side contacting a body and a liquid-impermeable back-side sheet (back sheet) positioned on a side opposite to that contacting the body.

Conventionally, there have been increasing demands for thinning and light-weighing of absorbent articles, from the viewpoint of designing property, convenience upon carrying, and efficiency upon distribution. Further, in the recent years, there have been growing needs for so-called eco-friendly intentions, in which resources are effectively utilized so that use of natural materials that require a long time to grow such as trees is avoided as much as possible, from the viewpoint of environmental protection. Conventionally, a method for thinning that is generally carried out in absorbent articles is, for example, a method of reducing hydrophilic fibers such as crushed pulp of a wood material, which has a role of fixing a water-absorbent resin in an absorbent material, while increasing a water-absorbent resin.

An absorbent material in which a water-absorbent resin having a smaller volume and higher water-absorbent capacity is used in a large amount with a lowered proportion of a hydrophilic fiber being bulky and having lower water-absorbent properties is intended to achieve thinning by reducing bulky materials while obtaining absorption capacity matching the design of an absorbent article, so that it is considered as a reasonable improved method. However, when distribution or diffusion of a liquid upon actually using in an absorbent article such as disposable diapers is considered, there is a disadvantage that if a large amount of the water-absorbent resin is formed into a soft gel-like state by absorption of the liquid, a so-called "gel-blocking phenomenon" takes place, whereby liquid diffusibility is markedly lowered and a liquid permeation rate of the absorbent material is slowed down. This "gel-blocking phenomenon" is a phenomenon in which especially when an absorbent material in which water-absorbent resins are highly densified absorbs a liquid, water-absorbent resins existing near a surface layer absorb the liquid to form soft gels that are even more densified near the surface layer, so that a liquid permeation into an internal of an absorbent material is blocked, thereby making the internal of the water-absorbent resin incapable of efficiently absorbing the liquid.

In view of the above, conventionally, as a means of inhibiting gel-blocking phenomenon which takes place by reducing hydrophilic fibers while using a water-absorbent resin in a large amount, for example, proposals such as a method using an absorbent polymer having such properties as specified Saline Flow Conductivity and Performance under Pressure (see Patent Publication 1), and a method using a water-absorbent resin prepared by heat-treating a specified water-absorbent resin precursor with a specified surface crosslinking agent (see Patent Publication 2) have been made.

However, in these methods, the liquid absorbent properties as absorbent materials in which water-absorbent resins are used in large amounts are not satisfactory. In addition, there arise some problems that the water-absorbent resin is subjected to be mobile before use or during use because hydrophilic fibers that play a role of fixing the water-absorbent resin are reduced. The absorbent material in which the localization of the absorbent resin takes place is more likely to cause gel-blocking phenomenon.

Further, an absorbent material of which hydrophilic fibers that contribute to retention of the form are reduced has a lowered shape-retaining ability as an absorbent material, so that deformation in shapes such as twist-bending or tear before or after the absorption of a liquid is likely to take place. An absorbent material with deformation in shapes has markedly lowered liquid diffusibility, so that abilities inherently owned by the absorbent material cannot be exhibited. In order to try to avoid such phenomena, a ratio of hydrophilic fibers and a water-absorbent resin would be limited, thereby posing limitations in the thinning of an absorbent article.

In view of the above, in recent years, as a next generation style absorbent material which is capable of increasing a content of a water-absorbent resin while using hydrophilic fibers in an absorbent material as little as possible, studies have been widely made on an absorbent laminate that substantially does not contain hydrophilic fibers in an absorbent layer, a water-absorbent sheet or the like. The studies include, for example, a method of keeping a water-absorbent resin in reticulation of a bulky nonwoven fabric (see Patent Publication 3), a method of sealing a water-absorbent polymer between two sheets of meltblown nonwoven fabrics (see Patent Publication 4), a method of interposing water-absorbent polymer particles between a hydrophobic nonwoven fabric and a hydrophilic sheet (see Patent Publication 5), and the like.

However, in a case where hydrophilic fibers are hardly used, the gel-blocking phenomenon as mentioned above is likely to take place. Even in a case where gel-blocking phenomenon does not take place, a thing that would serve the role of conventional hydrophilic fibers by which a body fluid such as urine is temporarily subjected to water retention and diffusion of the liquid to an overall absorbent material is lacking, so that a liquid leakage is likely to occur in the absorbent laminate, without being able to sufficiently capture the liquid.

Further, when an adhesive is used for retaining the shape of an absorbent laminate, the surface of a water-absorbent resin is coated with an adhesive, so that liquid absorbent properties are likely to be lowered. Alternatively, an upper side and a lower side of nonwoven fabrics are firmly adhered with an adhesive to confine an water-absorbent resin in a pouched form or the like, so that the water-absorbent properties inherently owned by the water-absorbent resin are less likely to be exhibited.

When adhesive strength of an absorbent laminate is weakened in order to improve liquid absorbent properties of the above-mentioned absorbent laminate, not only a large amount of the absorbent resin is detached upon working on the laminate, thereby making unfavorable economically, but also the laminate is exfoliated due to deficiency in adhesive strength, so that there are some possibilities of loss of commercial values. In other words, if the adhesion is strengthened, the gel-blocking phenomenon or liquid leakage occurs, and if the adhesion is weakened, it would lead to the detachment of a water-absorbent resin and the breaking of the laminate, so that an absorbent laminate or a water-absorbent sheet for which the above-mentioned problems are solved is not yet obtained at present.

Studies on improvement of the balance between adhesion and the liquid absorbent properties in the water-absorbent sheets as described above are also made. The studies include, for example, a method of using an absorbent laminate comprising two sheets of nonwoven fabrics adhered with reticular layers provided between the nonwoven fabrics, comprising upper and lower two layers of hot melt adhesives (see Patent Publication 6), a method of applying a specified reactive hot melt to a substrate made of a nonwoven fabric or a film, thereby fixing a water-absorbent resin (see Patent Publication 7), a method of coating a fine cellulose and a water-absorbent resin with a network-like hot melt to hold them (see Patent Publication 8), and the like. However, even if properties of a nonwoven fabric, a water-absorbent resin, and an adhesive, or conditions of use thereof are defined, it is difficult to obtain a water-absorbent sheet having high liquid absorbent properties and shape retaining ability. In addition, if a specified adhesive or method of adhesion is used, it is not desirable from the viewpoint of economical advantages and productivity, even if the liquid absorbent properties were improved.

There is also a method of immobilizing a water-absorbent resin to a substrate without using an adhesive. The method includes, for example, a method of adhering water-absorbent polymer particles in the process of polymerization to a synthetic fibrous substrate to carry out polymerization on the fibrous substrate (see Patent Publication 9), a method of polymerizing a monomer aqueous composition containing acrylic acid and an acrylic acid salt as main components on a nonwoven fabric substrate by means of electron beam irradiation (see Patent Publication 10), and the like.

In these methods, while the synthetic fibrous substrate is penetrated into the polymer particles to be firmly adhered, there are some disadvantages that it is difficult to complete the polymerization reaction in the substrate, so that unreacted monomers and the like remain in the substrate in large amounts.

PRIOR ART PUBLICATIONS

Patent Publications

Patent Publication 1: Japanese Unexamined Patent Publication No. Hei-9-510889
Patent Publication 2: Japanese Patent Laid-Open No. Hei-8-057311
Patent Publication 3: Japanese Unexamined Patent Publication No. Hei-9-253129
Patent Publication 4: Japanese Patent Laid-Open No. Hei-7-051315
Patent Publication 5: Japanese Patent Laid-Open No. 2002-325799
Patent Publication 6: Japanese Patent Laid-Open No. 2000-238161
Patent Publication 7: Japanese Unexamined Patent Publication No. 2001-158074
Patent Publication 8: Japanese Unexamined Patent Publication No. 2001-096654
Patent Publication 9: Japanese Patent Laid-Open No. 2003-011118
Patent Publication 10: Japanese Patent Laid-Open No. Hei-2-048944

SUMMARY OF THE INVENTION

Problems to be Solved by the Invention

In view of the above, an object of the present invention is to provide a water-absorbent sheet structure which is capable of avoiding the gel-blocking phenomenon even when the water-absorbent sheet structure contains a very small amount of pulps, so that the water-absorbent sheet structure has excellent fundamental properties (fast liquid permeation rate, sufficient water-retention capacity, small amount of liquid re-wet, small liquid leakage, and shape retaining ability), and is capable of accomplishing thinning.

Means to Solve the Problems

Specifically, the gist of the present invention relates to:
[1] a water-absorbent sheet structure comprising a structure in which an absorbent layer containing a water-absorbent resin (A) and a water-absorbent resin (B) is sandwiched with fibrous webs from an upper side and a lower side of the absorbent layer, characterized in that the water-absorbent resin (A) and the water-absorbent resin (B) are contained in a total amount of from 100 to 1,000 $g/m^2$, and that the water-absorbent resin (A) and the water-absorbent resin (B) have the following properties:
(1) the water-absorbent resin (A) having a water-retention capacity of saline solution (Ra) from 15 to 55 g/g;
(2) the water-absorbent resin (B) having a water-retention capacity of saline solution (Rb) from 10 to 50 g/g; and
(3) Ra and Rb mentioned above satisfies the relationship of the following formula: Ra−Rb≥(g/g);
[2] an absorbent article comprising the water-absorbent sheet structure as defined in the above [1], sandwiched between a liquid-permeable sheet and a liquid-impermeable sheet; and
[3] a water-absorbent resin composition containing a mixture of a water-absorbent resin (A) and a water-absorbent resin (B) having the following properties:
(1) the water-absorbent resin (A) having a water-retention capacity of saline solution (Ra) from 15 to 55 g/g;
(2) the water-absorbent resin (B) having a water-retention capacity of saline solution (Rb) from 10 to 50 g/g; and
(3) Ra and Rb mentioned above satisfies the relationship of the following formula: Ra−Rb≥(g/g)
wherein the water-absorbent resin (A) and the water-absorbent resin (B) are in a mass ratio, i.e. the water-absorbent resin (A):the water-absorbent resin (B), of from 98:2 to 50:50.

Effects of the Invention

The water-absorbent sheet structure according to the present invention exhibits some effects that a water-absorbent sheet structure has excellent shape retaining ability even when the structure is thin, so that the water-absorbent sheet structure does not undergo deformation of the form before liquid absorption or after the absorption, and is capable of sufficiently exhibiting absorbent properties. Therefore, the water-absorbent sheet structure according to the present invention is used for an absorbent material such as disposable diapers, whereby hygienic materials which are thin and have excellent design property, and at the same time not having disadvantages such as liquid leakage can be provided. Also, the water-absorbent sheet structure according to the present invention can be used in agricultural fields and fields of construction materials other than the field of hygienic materials.

MODES FOR CARRYING OUT THE INVENTION

Figure 1:
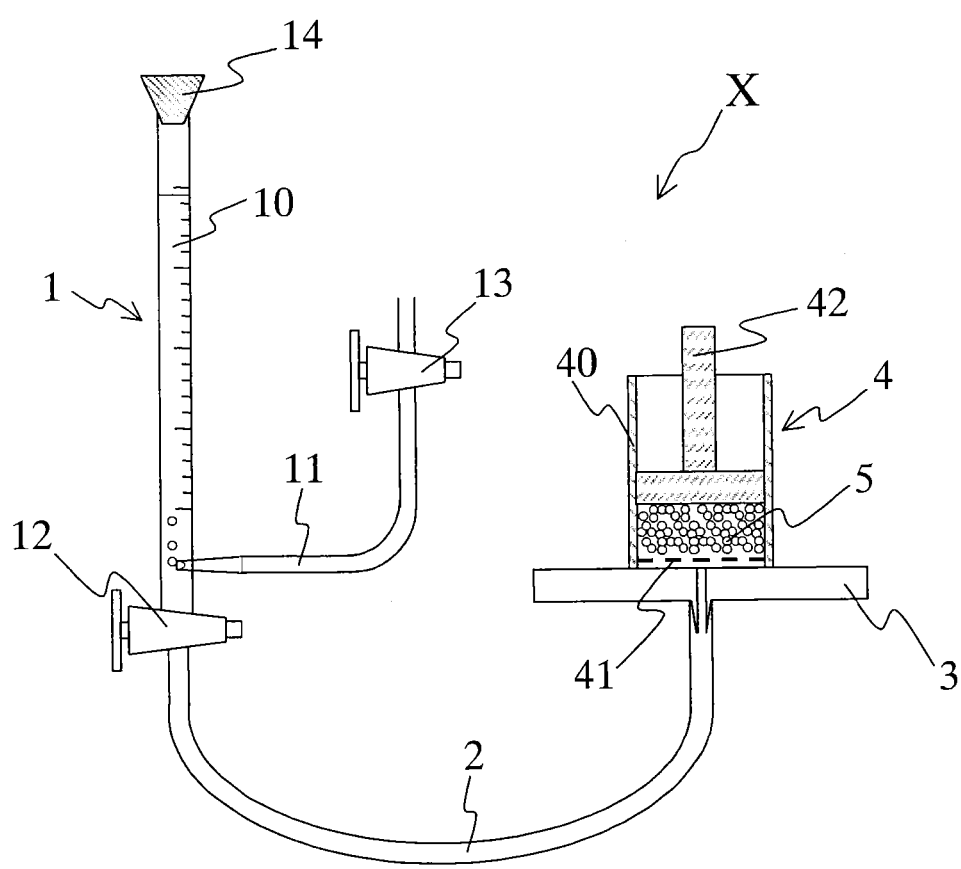
FIG. 1 A schematic view showing an outline of the constitution of an apparatus used for measuring a water-absorption capacity under load of a water-absorbent resin.

The water-absorbent sheet structure according to the present invention is a water-absorbent sheet structure comprising a structure in which an absorbent layer containing two kinds of water-absorbent resins (A) and (B) is sandwiched with fibrous webs. By forming an absorbent layer between the fibrous webs using the two kinds of the water-absorbent resins having specified properties in given amounts, a thin water-absorbent sheet structure which is capable of avoiding gel-blocking even with a small amount of hydrophilic fibers in the absorbent layer, and also has excellent liquid absorbent properties such as liquid permeability and small amount of liquid re-wet can be realized.

Further, in the water-absorbent sheet structure according to the present invention, a water-absorbent resin is appropriately adhered to fibrous webs by preferably a means such as adhesion, localization or scattering of the water-absorbent resin can be prevented, even when the water-absorbent resin substantially does not contain a hydrophilic fiber such as pulp fiber, and the shape retaining ability can also be favorably maintained.

The water-absorbent sheet structure according to the present invention may be in an embodiment where a hydrophilic fiber such as pulp fiber is admixed between the fibrous webs together with the water-absorbent resin in an amount that would not impair the effects of the present invention. However, it is preferable that the structure is in an embodiment where a hydrophilic fiber is substantially not contained, from the viewpoint of thinning.

As the kinds of the water-absorbent resins used in the present invention, commercially available water-absorbent resins can be used. For example, the water-absorbent resin includes hydrolysates of starch-acrylonitrile graft copolymers, neutralized products of starch-acrylic acid graft polymers, saponified products of vinyl acetate-acrylic acid ester copolymers, partially neutralized products of polyacrylic acid, and the like. Among these water-absorbent resins, the partially neutralized products of polyacrylic acids are preferred, from the viewpoint of production amount, production costs, water-absorbent properties, and the like. Methods for synthesizing partially neutralized products of polyacrylic acid include reversed phase suspension polymerization method, aqueous solution polymerization method, and the like. Among these polymerization methods, the water-absorbent resins obtained according to reversed phase suspension polymerization method are preferably used, from the viewpoint of excellent flowability of the resulting particles, smaller amounts of fine powder, high water-absorbent properties, such as liquid absorption capacity (expressed by indices such as water-retention capacity, effective amount of water absorbed, water-absorption capacity under load), and water-absorption rate.

The partially neutralized product of a polyacrylic acid has a degree of neutralization of preferably 50% by mol or more, and even more preferably from 70 to 90% by mol, from the viewpoint of increasing an osmotic pressure of the water-absorbent resin, thereby increasing water-absorbent properties.

The water-absorbent resin is contained in the water-absorbent sheet structure of from 100 to 1,000 g per one square-meter of the water-absorbent sheet structure, i.e. 100 to 1,000 $g/m^2$, preferably from 150 to 800 $g/m^2$, more preferably from 200 to 700 $g/m^2$, and even more preferably from 220 to 600 $g/m^2$, from the viewpoint of obtaining sufficient liquid absorbent properties even when a water-absorbent sheet structure according to the present invention is used for an absorbent article. It is required that the water-absorbent resin is contained in an amount of preferably 100 $g/m^2$ or more, from the viewpoint of exhibiting sufficient liquid absorbent properties as a water-absorbent sheet structure, thereby suppressing especially re-wetting, and it is required that the water-absorbent resin is contained in a total amount of preferably 1,000 $g/m^2$ or less, from the viewpoint of suppressing the gel-blocking phenomenon from being caused, exhibiting liquid diffusibility as a water-absorbent sheet structure, and further improving a liquid permeation rate.

The liquid absorbent properties of the water-absorbent sheet structure according to the present invention are influenced by the water-absorbent properties of the water-absorbent resin used. Therefore, it is preferable that the two kinds of the water-absorbent resins (A) and (B) to be used in the present invention are those selected with favorable ranges in water-absorbent properties such as liquid absorption capacity (expressed by indices such as water-retention capacity, effective amount of water absorbed and water-absorption capacity under load), and water-absorption rate, and mass-average particle size of the water-absorbent resin, by taking the constitution of each component of the water-absorbent sheet structure or the like into consideration.

In the present specification, the water-retention capacity of the two kinds of the water-absorbent resins (A) and (B) is evaluated as a water-retention capacity of saline solution. The water-absorbent resin has a water-retention capacity of saline solution satisfying each of the following ranges and relationships, from the viewpoint of absorbing a liquid in a larger amount, and preventing the gel-blocking phenomenon while keeping the gel strong during absorption. Further, the water-absorbent resin composition prepared by mixing the water-absorbent resin (A) and the water-absorbent resin (B) also satisfies each of the following ranges and relationships from the same viewpoint.

The water-absorbent resin (A) has a water-retention capacity (Ra) of saline solution of from 15 to 55 g/g, preferably from 20 to 55 g/g, more preferably from 25 to 55 g/g, even more preferably from 30 to 50 g/g, and still even more preferably from 30 to 45 g/g.

The water-absorbent resin (B) has a water-retention capacity (Rb) of saline solution of from 10 to 50 g/g, preferably from 10 to 45 g/g, more preferably from 10 to 40 g/g, even more preferably from 15 to 35 g/g, and still even more preferably from 15 to 30 g/g.

Ra and Rb mentioned above are those that satisfy the relationship of Ra−Rb≥5 g/g, preferably satisfy the relationship of Ra−Rb≥10 g/g, and more preferably satisfy the relationship of Ra−Rb≥15 g/g Here, the ranges of the a water-retention capacity of saline solution and a combination of the relationships of the above-mentioned water-absorbent resins (A) and (B) are arbitrary set, which are not particularly limited, and for example, the combinations include as follows.

The combination is Ra: 15 to 55 g/g, Rb: 10 to 50 g/g, and Ra−Rb≥5 g/g, preferably Ra: 20 to 55 g/g, Rb: 10 to 45 g/g, and Ra−Rb≥10 g/g, more preferably Ra: 25 to 55 g/g, Rb: 10 to 40 g/g, and Ra−Rb≥15 g/g, even more preferably Ra: 30 to 50 g/g, Rb: 15 to 35 g/g, and Ra−Rb≥15 g/g, and still even more preferably Ra: 30 to 45 g/g, Rb: 15 to 30 g/g, and Ra−Rb≥15 g/g.

The water-retention capacity of saline solution of the water-absorbent resin is a value obtainable by a measurement method described in Examples set forth below.

In addition, taking into consideration of a case where the water-absorbent sheet structure according to the present invention is used in absorbent articles such as disposable diapers, water-absorption capacity under load is also important, from the viewpoint that the one with a higher water-absorption capacity is preferred even in a state of being exposed to a load of absorbent article wearer. The water-absorbent resin has a water-absorption capacity of saline solution under load of 4.14 kPa is preferably 15 mL/g or more, more preferably from 20 to 40 mL/g, even more preferably from 23 to 35 mL/g, and still even more preferably from 25 to 32 mL/g. It is preferable that the water-absorbent resin (B) falls under the above-mentioned range, and it is more preferable that both the water-absorbent resins (A) and (B) fall under the above-mentioned range, from the viewpoint that the water-absorbent resin having a stronger strength of swelling a gel obtains flow pathways of the liquid, thereby preventing gel-blocking. The water-absorption capacity of saline solution under load of 4.14 kPa of the water-absorbent resin is a value obtainable by a measurement method described in Examples set forth below.

In the present specification, the water-absorption rate of the water-absorbent resin is evaluated as a water-absorption rate of saline solution. The water-absorbent resin has a water-absorption rate of saline solution of preferably 80 seconds or less, more preferably from 1 to 70 seconds, even more preferably from 2 to 60 seconds, and still even more preferably from 3 to 55 seconds, from the viewpoint of speeding up the liquid permeation rate of the water-absorbent sheet structure according to the present invention, thereby preventing a liquid leakage upon use in a hygienic material. In order to further increase the effects of the present invention, a difference between each of water-absorption rates (Sa) and (Sb) for the two kinds of the water-absorbent resins (A) and (B) satisfies such that Sa−Sb≥5 (seconds) is preferred, and that Sa−Sb≥10 (seconds) is more preferred. The water-absorption rate of the water-absorbent resin is a value obtainable by a measurement method described in Examples set forth below.

The water-absorbent resin used in the present invention has a mass-average particle size of preferably from 50 to 1000 μm, more preferably from 100 to 800 μm, and even more preferably from 200 to 600 μm, from the viewpoint of preventing the scattering of the water-absorbent resin and the gel-blocking phenomenon during water absorption of the water-absorbent resin in the water-absorbent sheet structure, and at the same time reducing the rugged feel of the water-absorbent sheet structure, thereby improving texture. The mass-average particle size of the water-absorbent resin is a value obtainable by a measurement method described in Examples set forth below.

In addition, it is preferable that the water-absorbent resin used in the present invention has, in addition to the water-absorption rate of saline solution within the range mentioned above, a given initial water-absorption rate and a given effective amount of water absorbed.

The initial water-absorption rate of the water-absorbent resin used in the present invention is expressed as an amount of water absorbed (mL) of a liquid per second in the water-absorption period of from 0 to 30 seconds, and the initial water-absorption rate is preferably 0.35 mL/s or less, from the viewpoint of suppressing the gel-blocking phenomenon from being caused at an initial stage of the liquid permeation in the water absorbent sheet structure, thereby accelerating liquid diffusion in an absorbent layer, and efficiently absorbing water in an even wider range of the water-absorbent resin. The initial water-absorption rate is more preferably from 0.05 to 0.30 mL/s, and even more preferably from 0.10 to 0.25 mL/s. The initial water-absorption rate is more preferably 0.05 mL/s or more, from the viewpoint of obtaining dry feel to skin in an initial stage of liquid permeation while diffusing the liquid. It is preferable that the water-absorbent resin (A) falls under the above-mentioned range, and it is more preferable that both the water-absorbent resins (A) and (B) fall under the above-mentioned range, from the viewpoint that the water-absorbent resin having a weaker strength of swelling a gel absorbs the liquid after diffusion, thereby preventing gel-blocking. The initial water-absorption rate of the water-absorbent resin is a value obtainable by a measurement method described in Examples set forth below.

In addition, the effective amount of water absorbed of the water-absorbent resin used in the present invention, in terms of an effective amount of water absorbed for saline solution, is preferably 25 mL/g or more, more preferably from 25 to 90 mL/g, even more preferably from 30 to 80 mL/g, and still even more preferably from 35 to 70 mL/g. The water-absorbent resin has an effective amount of water absorbed of preferably 25 mL/g or more, from the viewpoint of allowing a water-absorbent resin to absorb more liquid, and reducing the amount of re-wet, thereby obtaining dry feel, and the water-absorbent resin has an effective amount of water absorbed of preferably 90 mL/g or less, from the viewpoint of providing appropriate crosslinking of the water-absorbent resin, thereby keeping the gel strong upon absorption and preventing gel-blocking. The effective amount of water absorbed of the water-absorbent resin is a value obtainable by a measurement method described in Examples set forth below.

Generally, the water-absorption rate of the water-absorbent resin is likely to be slowed if an average particle size thereof becomes large. However, with regard to the initial water-absorption rate (mL/s), this effect is small even when an average particle size is made large in a conventional water-absorbent resin. Moreover, if a proportion of particles having larger sizes is made higher, it is undesirable because feel in the water-absorbent sheet structure is likely to be worsened. A method of controlling an initial water-absorption rate to a given range includes, for example, a method for producing a water-absorbent resin comprising increasing a crosslinking density of a water-absorbent resin with a crosslinking agent, or homogeneously coating a surface of a water-absorbent resin with a hydrophobic additive, or carrying out reversed phase suspension polymerization using a specified emulsifying agent, or the like.

However, if a crosslinking density of a water-absorbent resin is increased with a crosslinking agent, a given initial water-absorption rate might be satisfied but at the same time an effective amount of water absorbed of the water-absorbent resin is lowered, so that it is difficult to obtain a water-absorbent resin satisfying both a given initial water-absorption rate and a given effective amount of water absorbed.

Accordingly, a water-absorbent resin is preferably those in which a hydrophobic additive is homogeneously coated on a surface of a water-absorbent resin, and those produced according to reversed phase suspension polymerization using a specified emulsifying agent, from the viewpoint of facilitation in the production of a water-absorbent resin having both a given initial water-absorption rate and a given effective amount of water absorbed, among which the latter method is more preferred from the viewpoint of high water-absorbent properties. As a specified emulsifying agent, a nonionic surfactant having an appropriate hydrophobicity is preferably used, and a water-absorbent resin from a reversed phase suspension polymerization using them is obtained usually in a spherical or American football-shaped form, or an agglomerated form thereof. The resin having the above form is preferably used from the viewpoint that pulverization is hardly needed, and has excellent flowability as powder and excellent workability during the production of a water-absorbent sheet structure.

The water-absorbent resin (A) and the water-absorbent resin (B), to be used in the absorbent layers of the water-absorbent sheet structure, are in a mass ratio, i.e. the water-absorbent resin (A):the water-absorbent resin (B), and the water-absorbent resin composition according to the present invention has the same mass ratio, of preferably from 98:2 to 50:50, more preferably from 95:5 to 60:40, even more preferably from 90:10 to 70:30, and still even more preferably from 90:10 to 80:20, from the viewpoint of increasing the liquid absorbent properties of the water-absorbent sheet structure. The proportion of the water-absorbent resin (A) having a high water-retention capacity is preferably 50 or more, from the viewpoint of reducing an amount of re-wet after the water-absorbent sheet structure is allowed to absorb the liquid, and the proportion of the water-absorbent resin (B) having a high gel-swelling strength is preferably 2 or more, in other words, the proportion of the water-absorbent resin (A) is preferably 98 or less, from the viewpoint of obtaining flow pathway of the liquid and preventing gel-blocking.

Although the reasons why the water-absorbent sheet structure according to the present invention has high liquid absorbent properties despite the fact that the water-absorbent sheet structure is thin and contains a small amount of hydrophilic fiber as compared to the conventional water-absorbent sheet structures are not elucidated, they are deduced as follows. In the water-absorbent sheet structure having a structure in which the water-absorbent resin is sandwiched with fibrous webs, if the water-absorbent resin (A) alone, which does not have a high gel-swelling strength while having a high water-retention capacity, is used, the gel after water absorption is likely to be deformed, so that there is a risk of causing the gel-blocking mentioned above. On the other hand, if the water-absorbent resin (B) alone, which has a high gel-swelling strength while having a low water-retention capacity, is used, the absorption capacity of the water-absorbent sheet structure would be lowered, so that there is a risk that an amount of re-wet after the liquid absorption becomes large. In view of the above, in the water-absorbent sheet structure having a structure in which the water-absorbent resins are sandwiched with fibrous webs, since the water-absorbent resin (A), which does not have a high gel-swelling strength while having a high water-retention capacity, is blended with the water-absorbent resin (B), which has a high gel-swelling strength while having a low water-retention capacity, in proper amounts, a part of the resin is allowed to swell with a high strength in the absorbent layer, and thereby the flow pathway of the liquid is obtained and the gel-blocking can be avoided, so that it is considered that a water-absorbent sheet structure having excellent liquid diffusibility and a small amount of re-wet is obtained.

The fibrous webs used in the present invention are not particularly limited, as long as the fibrous webs are known webs in which fibers are formed into a sheet-like form. The fibrous webs include nonwoven fabrics made of polyolefin fibers such as polyethylene (PE) and polypropylene (PP), polyester fibers such as polyethylene terephthalate (PET), polytrimethylene terephthalate (PTT), and polyethylene naphthalate (PEN), polyamide fibers such as nylon; rayon fibers, and other synthetic fibers; nonwoven fabrics produced by mixing cotton, silk, hemp, pulp (cellulose) fibers; sanitary papers such as tissue paper, toilet paper, and towel paper, or the like, from the viewpoint of liquid permeability, flexibility and strength upon forming into a water-absorbent sheet structure. Among these fibrous webs, nonwoven fabrics made of synthetic fibers are preferably used, from the viewpoint of increasing the strength of the water-absorbent sheet structure. Especially, nonwoven fabrics made of rayon fibers, polyolefin fibers, and polyester fibers are preferred. These nonwoven fabrics may be nonwoven fabrics made of single fibers mentioned above, or nonwoven fabrics made of two or more kinds of fibers used in combination.

More specifically, spunbond nonwoven fabrics made of fibers selected from the group consisting of polyolefin fibers, polyester fibers and blends thereof are more preferred, from the viewpoint of obtaining shape retaining ability of the water-absorbent sheet structure, and preventing pass of the water-absorbent resin through the nonwoven fabric. In addition, spunlace nonwoven fabrics made of rayon fibers as a main component are also more preferred as the fibrous webs used in the present invention, from the viewpoint of even more increasing liquid absorbent properties and flexibility upon formation of the sheet. Among the spunbond nonwoven fabrics mentioned above, spunbond-meltblown-spunbond (SMS) nonwoven fabrics and spunbond-meltblown-meltblown-spunbond (SMMS) nonwoven fabrics, which have a multi-layered structure of polyolefin fibers are more preferably used, and the SMS nonwoven fabrics and the SMMS nonwoven fabrics each made of polypropylene fibers as a main component are especially preferably used. On the other hand, as the above-mentioned spunlace nonwoven fabrics, those of proper blends of main component rayon fibers with polyolefin fibers and/or polyester fibers are preferably used, and among them, rayon-PET nonwoven fabrics and rayon-PET-PE nonwoven fabrics are preferably used. The above-mentioned nonwoven fabrics may contain a small amount of pulp fibers to an extent that would not increase the thickness of the water-absorbent sheet structure.

When the hydrophilicity of the above-mentioned fibrous web is too low, the liquid absorbent properties of the water-absorbent sheet structure is worsened, and on the other hand, when the hydrophilicity is much higher than a necessary level, the liquid absorbent properties would not be improved to the level equivalent thereto. Therefore, it is desired that the fibrous web has an appropriate level of hydrophilicity. From those viewpoints, the fibrous webs having a degree of hydrophilicity of from 5 to 200 are preferably used, more preferably those having a degree of hydrophilicity of from 8 to 150, even more preferably those having a degree of hydrophilicity of from 10 to 100, and still even more preferably those having a degree of hydrophilicity of from 12 to 80 when measured in accordance with the method for measuring "Degree of Hydrophilicity of Fibrous Webs" described later. The fibrous web having hydrophilicity as mentioned is not particularly limited, and among the fibrous webs mentioned above, those of which materials themselves show hydrophilicity such as rayon fibers may be used, or those obtained by subjecting hydrophobic chemical fibers such as polyolefin fibers or polyester fibers to a hydrophilic treatment according to a known method to give an appropriate degree of hydrophilicity may be used. The method of hydrophilic treatment includes, for example, a method including subjecting, in a spunbond nonwoven fabric, a mixture of a hydrophobic chemical fiber with a hydrophilic treatment agent to a spunbond method to give a nonwoven fabric; a method including carrying a hydrophilic treatment agent along upon the preparation of a spunbond nonwoven fabric with a hydrophobic chemical fiber; or a method including obtaining a spunbond nonwoven fabric with a hydrophobic chemical fiber, and thereafter impregnating the nonwoven fabric with a hydrophilic treatment agent, and the like. As the hydrophilic treatment agent, an anionic surfactant such as an aliphatic sulfonic acid salt or a sulfuric acid ester of a higher alcohol; a cationic surfactant such as a quaternary ammonium salt; a nonionic surfactant such as a polyethylene glycol fatty acid ester, a polyglycerol fatty acid ester, or a sorbitan fatty acid ester; a silicone-based surfactant such as a polyoxyalkylene-modified silicone; and a stain-release agent made of a polyester-based, polyamide-based, acrylic, or urethane-based resin; or the like is used.

It is preferable that the fibrous webs that sandwich the absorbent layer is hydrophilic, from the viewpoint of even more increasing the liquid absorbent properties of the water-absorbent sheet structure. Especially from the viewpoint of preventing slope liquid leakage, it is more preferable that hydrophilic property of a nonwoven fabric used in a lower side of an absorbent layer is equivalent to or higher than hydrophilic property of a nonwoven fabric used in an upper side of the absorbent layer. The upper side of an absorbent layer as used herein refers to a side to which a liquid to be absorbed is supplied at the time of preparing an absorbent article using the water-absorbent sheet structure obtained, and the lower side of an absorbent layer refers to a side opposite thereof.

The fibrous web is preferably a fibrous web having an appropriate bulkiness and a large basis weight, from the viewpoint of giving the water-absorbent sheet structure according to the present invention excellent liquid permeability, flexibility, strength and cushioning property, and speeding up the liquid permeation rate of the water-absorbent sheet structure. The fibrous web has a basis weight of preferably from 5 to 300 g/m$^2$, more preferably from 10 to 200 g/m$^2$, even more preferably from 11 to 100 g/m$^2$, and still even more preferably from 13 to 50 g/m$^2$. Also, the fibrous web has a thickness of preferably in the range of from 20 to 800 μm, more preferably in the range of from 50 to 600 μm, and even more preferably in the range of from 80 to 450 μm.

It is preferable that the absorbent layer further contains an adhesive, from the viewpoint of increasing shape retaining ability of the water-absorbent sheet structure obtained. When an adhesive is used in the present invention, the adhesive includes, for example, rubber-based adhesives such as natural rubbers, butyl rubbers, and polyisoprene; styrene-based elastomer adhesives such as styrene-isoprene block copolymers (SIS), styrene-butadiene block copolymers (SBS), styrene-isobutylene block copolymers (SIBS), and styrene-ethylene-butylene-styrene block copolymers (SEBS); ethylene-vinyl acetate copolymer (EVA) adhesives; ethylene-acrylic acid derivative copolymer-based adhesives such as ethylene-ethyl acrylate copolymer (EEA), and ethylene-butyl acrylate copolymer (EBA); ethylene-acrylic acid copolymer (EAA) adhesives; polyamide-based adhesives such as copolymer nylons and dimer acid-based polyamides; polyolefin-based adhesives such as polyethylenes, polypropylenes, atactic polypropylenes, and copolymeric polyolefins; polyester-based adhesives such as polyethylene terephthalate (PET), polybutylene terephthalate (PBT), and copolymeric polyesters; and acrylic-based adhesives. In the present invention, the ethylene-vinyl acetate copolymer adhesives, the styrene-based elastomer adhesives, the polyolefin-based adhesives, and the polyester-based adhesives are preferred, from the viewpoint of high adhesive strength, thereby making it possible to prevent exfoliation of a fibrous web and scattering of the water-absorbent resin in the water-absorbent sheet structure. These adhesives may be used alone, or they may be used in combination of two or more kinds.

When a thermal-fusing adhesive is used, the adhesive has a melting temperature (softening temperature) of preferably from 60° to 180° C., more preferably from 70° to 150° C., and even more preferably from 75° to 125° C., from the viewpoint of sufficiently fixing a water-absorbent resin to a fibrous web, and at the same time preventing thermal deterioration or deformation of the fibrous web.

When the adhesive is used in the water-absorbent sheet structure, the adhesive is contained in a proportion preferably in the range of from 0.05 to 2.0 times, more preferably in the range of from 0.08 to 1.5 times, and even more preferably in the range of from 0.1 to 1.0 time the amount of the water-absorbent resin contained (mass basis). It is preferable that the adhesive is contained in a proportion of 0.05 times or more, from the viewpoint of having sufficient adhesion, thereby preventing exfoliation of the fibrous webs themselves or scattering of the water-absorbent resin, and increasing shape retaining ability of a water-absorbent sheet structure. It is preferable that the adhesive is contained in a proportion of 2.0 times or less, from the viewpoint of avoiding the inhibition of the swelling of the water-absorbent resin due to too strong adhesion to each other, thereby improving a permeation rate or liquid leakage of a water-absorbent sheet structure.

In the water-absorbent sheet structure according to the present invention, the absorbent layer formed between the fibrous webs contains at least water-absorbent resins, and the absorbent layer is formed by, for example, evenly dispersing a mixed powder of water-absorbent resins and an adhesive on a fibrous web, further overlaying with a fibrous web, and subjecting overlaid layers to heating, if necessary, heating under pressure, near a melting temperature of the adhesive. Alternatively, the absorbent layer is formed by evenly dispersing water-absorbent resins over an adhesive-coated fibrous web, further overlaying with an adhesive-coated fibrous web, and subjecting overlaid layers to heating, if necessary, under pressure, or the absorbent layer is also formed by sandwiching water-absorbent resins with fibrous webs, and thereafter subjecting the overlaid layers to thermal calendaring or thermal embossing or the like.

The water-absorbent sheet structure according to the present invention can be produced by a method, for example, as described in a method given hereinbelow.

(a) A mixed powder of two kinds of water-absorbent resins and an adhesive (water-absorbent resin composition) is evenly dispersed over a fibrous web, another fibrous web is overlaid thereto, and the overlaid layers are subjected to pressing while heating near a melting temperature of the adhesive.

(b) A mixed powder of two kinds of water-absorbent resins and an adhesive (water-absorbent resin composition) is evenly dispersed over a fibrous web, and passed through a heating furnace to fix the powder to an extent that the powder does not scatter. A fibrous web is overlaid thereto, and the overlaid layers are subjected to pressing while heating.

(c) An adhesive is melt-coated over a fibrous web, a mixture of water-absorbent resins (water-absorbent resin composition) is immediately thereafter evenly dispersed thereto to form a layer, and another fibrous web to which an adhesive is melt-coated is overlaid from an upper side in a manner that a coated side of the adhesive is facing the side of the dispersed water-absorbent resin, and the overlaid layers are subjected to pressing, or pressing, if necessary, with heating, using a roller press or the like.

(d) A mixed powder of two kinds of water-absorbent resins (water-absorbent resin composition) is evenly dispersed over a fibrous web, another web is overlaid thereto, and the overlaid layers are subjected to thermal embossing, thereby pressing the fibrous webs themselves to each other while heating.

A water-absorbent sheet structure having a structure in which an absorbent layer containing water-absorbent resins and an adhesive is sandwiched with two sheets of fibrous webs can be obtained by, for example, producing a water-absorbent sheet structure according to the method shown in any one of these (a) to (d). Among them, the methods of (a), (c) and (d) are more preferred, from the viewpoint of convenience in the production method and high production efficiency.

Here, the water-absorbent sheet structure can also be produced by using the methods exemplified in (a) to (d) in combination. The water-absorbent sheet structure may be additionally subjected to embossing treatment during the pressing while heating in the production of a sheet or after the production of the sheet, for the purposes of improving the feel and improving liquid absorbent properties of the water-absorbent sheet structure.

In addition, the water-absorbent sheet structure according to the present invention may properly be formulated with an additive such as a deodorant, an anti-bacterial agent, or a gel stabilizer In the water-absorbent sheet structure according to the present invention, the water-absorbent sheet structure has a peeling strength in a specified range of preferably from 0.05 to 3.0 N/7 cm, more preferably from 0.1 to 2.5 N/7 cm, even more preferably from 0.15 to 2.0 N/7 cm, and still even more preferably from 0.2 to 1.5 N/7 cm. When the water-absorbent sheet structure has a peeling strength exceeding 3.0 N/7 cm, the adhesion of the absorbent layer is too strong, so that an effect of adding a given amount of a water-absorbent resin having specified water absorbent properties is less likely to be obtained. When the water-absorbent sheet structure has a peeling strength of less than 0.05 N/7 cm, the adhesion of the absorbent layer is too weak, so that the water-absorbent sheet structure has worsened shape retaining ability while the action of the water-absorbent resin is not inhibited, thereby allowing migration of the water-absorbent resin and exfoliation of the fibrous webs, and whereby it is more likely to be difficult to work into absorbent articles such as disposable diapers. In the present specification, the peeling strength of the water-absorbent sheet structure is a value obtainable by a measurement method described in Examples set forth below.

Taking into consideration of the use of the water-absorbent sheet structure according to the present invention in disposable diapers and the like, the water-absorbent sheet structure has a water-retention capacity of saline solution of preferably from 500 to 45,000 g/m$^2$, more preferably from 900 to 33,000 g/m$^2$, and even more preferably from 1,500 to 25,000 g/m$^2$, from the viewpoint that it is preferable that the water-absorbent resin contained therein exhibits sufficient water-absorbent properties, so that the water-absorbent sheet structure has an even higher liquid absorption capacity. In the present specification, the water-retention capacity of saline solution of the water-absorbent sheet structure is a value obtainable by a measurement method described in Examples set forth below.

Further, a water-retention capacity of saline solution A [g/m$^2$] of the water-absorbent sheet structure preferably satisfies a relational formula: $0.5 \times B \times C \leq A \leq 0.9 \times B \times C$, more preferably satisfying a relational formula: $0.55 \times B \times C \leq A \leq 0.85 \times B \times C$, and even more preferably satisfying a relational formula: $0.6 \times B \times C \leq A \leq 0.8 \times B \times C$, based on the amount B [g/m$^2$] of the above-mentioned water-absorbent resin contained and the water-retention capacity C [g/g] of the above-mentioned water-absorbent resin, from the viewpoint that it is preferable that the water-absorbent resin is immobilized between the fibrous webs by a means for an appropriate adhesion to an extent that the water-absorbent properties of the water-absorbent resin are not largely inhibited.

In the present invention, the above-mentioned water-absorbent sheet structure can also take a structure in which a part or entire side of the absorbent layer thereof is fractionated by using an appropriate breathable fractionating layer, into an upper side primary absorbent layer and a lower side secondary absorbent layer in a perpendicular direction (the thickness direction of the sheet). By having the above structure, the liquid absorbent properties of the water-absorbent sheet structure, especially slope liquid leakage, is dramatically improved.

The breathable fractionating layer has appropriate breathability and liquid-permeability, which may be a layer in which a particle-form substance such as a water-absorbent resin does not substantially pass therethrough. Specific examples thereof include reticular products such as nets having fine pores made of PE or PP fibers; porous films such as perforated films; sanitary papers such as tissue paper; and cellulose-containing synthetic fiber nonwoven fabrics such as air laid nonwoven fabrics made of pulp/PE/PP, or nonwoven fabrics made of synthetic fibers, such as rayon fibers, polyolefin fibers, and polyester fibers. Among them, the same fibrous webs as those used in sandwiching the absorbent layer in the present invention are preferably used, from the viewpoint of the properties of the water-absorbent sheet structure obtained.

The water-absorbent resin in the secondary absorbent layer is used in an amount of preferably in the range of from 0.01 to 1.0 time, more preferably in the range of from 0.05 to 0.8 times, and even more preferably in the range of from 0.1 to 0.5 times the amount of the water-absorbent resin used of the primary absorbent layer (mass ratio). The water-absorbent resin in the secondary absorbent layer is used in an amount of preferably 0.01 times or more, from the viewpoint of sufficiently exhibiting liquid absorbent properties of the secondary absorbent layer, and preventing liquid leakage, and the water-absorbent resin is used in an amount of preferably 1.0 time or less, from the viewpoint of increasing dry feel at the surface after the liquid absorption and reducing amount of re-wet.

The liquid absorbent properties of the water-absorbent sheet structure according to the present invention are influenced by the water-absorbent properties of the water-absorbent resin used. Therefore, it is preferable that the water-absorbent resin of the primary absorbent layer to be used in the present invention is those selected with favorable ranges in water-absorbent properties such as liquid absorption capacity (expressed by indices such as water-retention capacity, effective amount of water absorbed and water-absorption capacity under load), and water-absorption rate, and mass-average particle size of the water-absorbent resin, by taking the constitution of each component of the water-absorbent sheet structure or the like into consideration. In addition, the water-absorbent resin of the secondary absorbent layer may be identical to the water-absorbent resin of the primary absorbent layer, or may be those within the range described later.

More specifically, an embodiment where a water-absorbent resin used in at least one of the absorbent layers is a water-absorbent resin obtained by reversed phase suspension polymerization method is preferred, an embodiment where a water-absorbent resin used in a secondary absorbent layer is a water-absorbent resin obtained by reversed phase suspension polymerization method is more preferred, and an embodiment where both the water-absorbent resins used in the primary absorbent layer and the secondary absorbent layer are water-absorbent resins obtained by reversed phase suspension polymerization method is even more preferred.

Here, the water-retention capacity of saline solution, the water-absorption capacity of saline solution under load of 4.14 kPa, the water-absorption rate of saline solution, the effective amount of water absorbed, the mass-average particle size, and the like of the water-absorbent resin used in the secondary absorbent layer are not particularly limited, and those within the same ranges as in the above-mentioned primary absorbent layer are used.

The water-absorbent sheet structure according to the present invention has one feature in the viewpoint of enabling thinning of the sheet. When the use in absorbent articles is taken into consideration, the water-absorbent sheet structure has a thickness, in a dry state, of preferably 5 mm or less, more preferably 4 mm or less, even more preferably from 0.5 to 3 mm, and still even more preferably from 0.8 to 2 mm. The dry state refers to a state before which the water-absorbent sheet structure absorbs a liquid. In the present specification, the thickness of the water-absorbent sheet structure in a dry state is a value obtainable by a measurement method described in Examples set forth below.

Further, the water-absorbent sheet structure according to the present invention has one feature in that a liquid has a fast permeation rate, and the water-absorbent sheet structure has a total permeation rate of preferably 120 seconds or less, more preferably 100 seconds or less, and even more preferably 90 seconds or less, when its use in an absorbent article is taken into consideration. In the present specification, the total permeation rate of the water-absorbent sheet structure is a value obtainable by a measurement method described in Examples set forth below.

Further, the water-absorbent sheet structure according to the present invention has one feature in that a liquid has smaller slope liquid leakage, and the water-absorbent sheet structure has a leakage index of preferably 150 or less, more preferably 100 or less, and even more preferably 50 or less, when its use in an absorbent article is taken into consideration. In the present specification, the leakage index of the water-absorbent sheet structure is a value obtainable by a measurement method described in Examples set forth below.

Further, the water-absorbent sheet structure according to the present invention has one feature that an amount of re-wet after the liquid permeation is small. The amount of re-wet of the liquid in the water-absorbent sheet structure is preferably 12 g or less, more preferably 10 g or less, and even more preferably 8 g or less, when its use in an absorbent article is taken into consideration. In the present specification, the amount of re-wet of the liquid in the water-absorbent sheet structure is a value obtainable by a measurement method described in Examples set forth below.

Further, since the water-absorbent sheet structure according to the present invention has a very small amount of a material derived from nature, consideration has been made to the environment while having high performance in thickness, permeation rate, and a leakage index as mentioned above. The proportion of the natural material used is preferably 30% by mass or less, more preferably 20% by mass or less, even more preferably 15% by mass or less, and still even more preferably 10% by mass or less. The proportion of the natural material used is calculated by dividing a total content of pulp, cotton, hemp, silk, and the like contained in very small amounts as the constituents of the water-absorbent sheet structure by mass of the water-absorbent sheet structure.

EXAMPLES

The present invention will be specifically described hereinbelow by the Examples, without intending to limit the scope of the present invention thereto.

The properties of the water-absorbent resin and the water-absorbent sheet structure were measured and evaluated in accordance with the following methods.

<Water-Retention Capacity of Saline Solution of Water-Absorbent Resin>

The amount 2.0 g of water-absorbent resin was weighed in a cotton bag (Cottonbroad No. 60, width 100 mm×length 200 mm), and placed in a 500 mL-beaker. Saline solution (0.9% by mass aqueous solution of sodium chloride, hereinafter referred to the same) was poured into the cotton bag in an amount of 500 g at one time, and the saline solution was dispersed so as not to cause an unswollen lump of the water-absorbent resin. The upper part of the cotton bag was tied up with a rubber band, and the cotton bag was allowed to stand for 1 hour, to sufficiently make the water-absorbent resin swollen. The cotton bag was dehydrated for 1 minute with a dehydrator (manufactured by Kokusan Enshinki Co., Ltd., product number: H-122) set to have a centrifugal force of 167 G. The mass Wa (g) of the cotton bag containing swollen gels after the dehydration was measured. The same procedures were carried out without adding water-absorbent resin, and the empty mass Wb (g) of the cotton bag upon wetting was measured. The water-retention capacity of saline solution of the water-absorbent resin was calculated from the following formula.

Water-Retention Capacity of Saline

Solution (g/g) of Water-Absorbent Resin =

$[Wa - Wb]$ (g)/Mass (g) of Water-Absorbent Resin

<Water-Absorption Capacity of Saline Solution of Water-Absorbent Resin Under Load of 4.14 kPa>

The water-absorption capacity of saline solution of water-absorbent resin under load of 4.14 kPa was measured using a measurement apparatus X of which outline constitution was shown in FIG. 1.

The measurement apparatus X shown in FIG. 1 comprised a burette section 1, a lead tube 2, a measuring platform 3, and a measuring section 4 placed on the measuring platform 3. The burette section 1 was connected to a rubber plug 14 at the top of a burette 10, and an air inlet tube 11 and a cock 12 at the bottom portion thereof, and the burette section further had a cock 13 at the top portion of the air inlet tube 11. The lead tube 2 was attached between the burette section 1 and the measuring platform 3. The lead tube 2 had a diameter of 6 mm. A hole of a diameter of 2 mm was made at the central section of the measuring platform 3, and the lead tube 2 was connected thereto. The measuring section 4 had a cylinder 40, a nylon mesh 41 adhered to the bottom part of the cylinder 40, and a weight 42. The cylinder 40 had an inner diameter of 2.0 cm. The nylon mesh 41 had an opening of 200 mesh (sieve opening: 75 μm), and moreover, a given amount of the water-absorbent resin 5 was evenly spread over the nylon mesh 41. The weight 42 had a diameter of 1.9 cm and a mass of 119.6 g. This weight 42 was placed on the water-absorbent resin 5, so that load of 4.14 kPa could be evenly applied to the water-absorbent resin 5.

The measurements of water-absorption capacity of saline solution under load of 4.14 kPa using the measurements apparatus X were carried out in accordance with the following procedures. The measurements were taken indoors at a temperature of 25° C. and humidity of from 45 to 75%. First, the cock 12 and the cock 13 at the burette section 1 were closed, and a saline solution adjusted to 25° C. was poured from the top of the burette 10 and the top of the burette was tightly plugged with the rubber plug 14. Thereafter, the cock 12 and the cock 13 at the burette section 1 were opened. Next, the height of the measuring platform 3 was adjusted so that the end of the lead tube 2 in the central section of the measuring platform 3 and an air introduction port of the air inlet tube 11 were at the same height.

On the other hand, 0.10 g of the water-absorbent resin 5 was evenly spread over the nylon mesh 41 in the cylinder 40, and the weight 42 was placed on the water-absorbent resin 5. The measuring section 4 was placed so that its center was in alignment with a lead tube port in the central section of the measuring platform 3.

The volume reduction of the saline solution in the burette 10, i.e., the volume of the saline solution absorbed by the water-absorbent resin 5, Wc (mL), was continuously read off, from a time point where the water-absorbent resin 5 started absorbing water.

In the measurement using the measurement apparatus X, the water-absorption capacity of saline solution under load of the water-absorbent resin 5 after 60 minutes passed from a time point of starting water absorption was calculated by the following formula.

Water-Absorption Capacity of Saline Solution Under Load of 4.14 kPa (mL/g) of Water-Absorbent Resin=Wc (mL)÷0.10 (g)

<Initial Water-Absorption Rate and Effective Amount of Water Absorbed of Water-Absorbent Resin>

Figure 2:
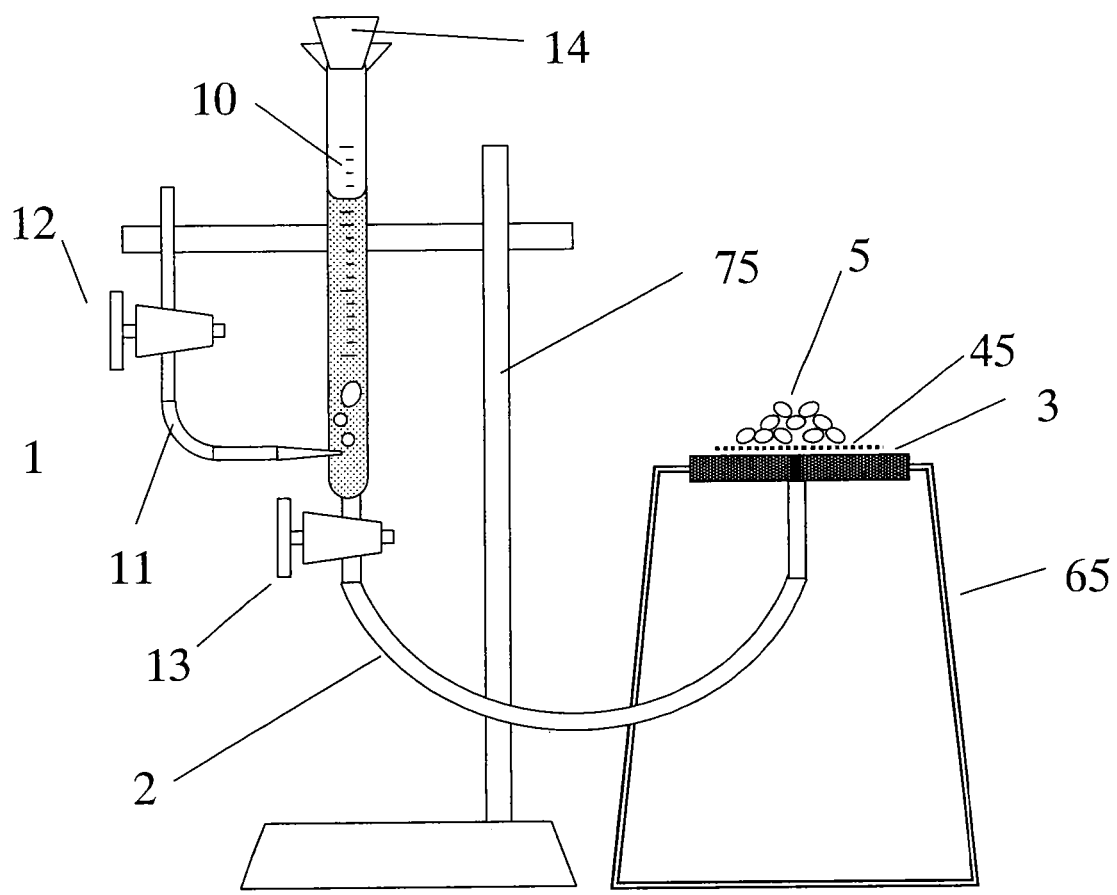
FIG. 2 A schematic view showing an outline of the constitution of an apparatus used for measuring an initial water-absorption rate and an effective amount of water absorbed of a water-absorbent resin.

The initial water-absorption rate and the effective amount of water absorbed of the water-absorbent resin were measured using a measurement apparatus as shown in FIG. 2.

The measurement apparatus comprised a burette section 1, a lead tube 2, a measuring platform 3, a nonwoven fabric 45, a stand 65, and a clamp 75. The burette section 1 was connected to a rubber plug 14 at the top of a burette 10 which had been graduated in units of 0.1 mL, and an air inlet tube 11 and a cock 12 at the bottom portion thereof, and further, the burette 10 had a cock 13 at a tip end of bottom portion thereof. The burette section 1 was fixed with a clamp 75. The lead tube 2 was attached between the burette section 1 and the measuring platform 3, and the lead tube 2 had an inner diameter of 6 mm. A hole of a diameter of 2 mm was made at the central section of the measuring platform 3, and the lead tube 2 was connected thereto. The measuring platform 3 was supported at an appropriate height by a stand 65.

The measurements of the initial water-absorption rate and the effective amount of water absorbed using the measurement apparatus as described above were carried out by the following procedures. The measurements were taken indoors at a temperature of 25° C. and humidity of from 45 to 75%. First, the cock 12 and the cock 13 at the burette section 1 were closed, and saline solution adjusted to 25° C. was poured from the top of the burette 10 and the top of the burette was tightly plugged with the rubber plug 14. Thereafter, the cock 12 and the cock 13 at the burette section 1 were opened. Next, an internal of a lead tube 2 was filled with saline solution while removing bubbles, and the height of the measuring platform 3 was adjusted so that a water level of the saline solution coming out of a lead tube inlet at the central portion of the measuring platform 3 and an upper side of the measuring platform 3 would be at the same height.

Next, a nonwoven fabric 45 cut into dimensions of 30 mm×30 mm (hydrophilic rayon spunlace having a basis weight of 25 g/m$^2$) was spread on a lead tube inlet at the central portion of the measuring platform 3, and the nonwoven fabric was allowed to absorb water until reaching an equilibrium. In the state where a nonwoven fabric absorbed water, the generation of bubbles from an air lead tube 11 to a burette 10 was observed, and having confirmed that the generation of bubbles stopped within several minutes, it was judged that an equilibrium was reached. After equilibration, the scales of the burette 10 were read off to confirm a zero point.

Separately, 0.10 g of a water-absorbent resin 5 was measured accurately, and supplied at one time to a central part of a nonwoven fabric 45. An amount of saline solution reduced inside the burette 10 (in other words, an amount of saline solution absorbed by the particles of a water-absorbent resin 5) was properly read off, and a reduced portion of saline solution after 30 seconds counted from the supplying of a water-absorbent resin 5 Wd (mL) was recorded as an amount of water absorbed per 0.10 g of a water-absorbent resin. Here, the measurements of the reduced portion were continued to be taken even after the passage of 30 seconds, and the measurements were completed after 30 minutes. The measurements were taken 5 times per one kind of a water-absorbent resin, and a 3-point average excluding a minimum value and a maximum value was used at values after the passage of 30 seconds.

The amount of saline solution reduced inside the burette 10 (the amount of saline solution absorbed by a water-absorbent resin 5) Wd (mL) after 30 seconds from the supply of a water-absorbent resin 5 was converted to an amount of water absorbed per 1 g of a water-absorbent resin, and a quotient obtained by further dividing the resulting converted value by 30 (seconds) was defined as an initial water-absorption rate (mL/s) of the water-absorbent resin. In other words, the initial water-absorption rate (mL/s)=Wd÷(0.10×30).

In addition, an amount of saline solution reduced inside the burette 10 (an amount of saline solution absorbed by a water-absorbent resin 5) We (mL) after the passage of 30 minutes from the supply of a water-absorbent resin 5 was converted to an amount of water absorbed per 1 g of a water-absorbent resin, and defined as an effective amount of water absorbed (mL/g) of saline solution of the water-absorbent resin. In other words, the effective amount of water absorbed (mL/g)=We÷0.10.

<Water-Absorption Rate of Saline Solution of Water-Absorbent Resin>

This test was conducted indoors temperature-controlled to 25°±1° C. The amount 50±0.1 g of saline solution was weighed out in a 100 mL beaker, and a magnetic stirrer bar (8 mmφ×30 mm, without a ring) was placed therein. The beaker was immersed in a thermostat, of which liquid temperature was controlled to 25°±0.2° C. Next, the beaker was placed over the magnetic stirrer so that a vortex was generated in saline solution at a rotational speed of 600 r/min, the water-absorbent resin was then quickly added in an amount of 2.0±0.002 g to the above beaker, and the time period (seconds) from a point of addition of the water-absorbent resin to a point of convergence of the vortex of the liquid surface was measured with a stopwatch, which was defined as a water absorption rate of the water-absorbent resin.

<Mass-Average Particle Size of Water-Absorbent Resin>

An amorphous silica (Sipernat 200, Degussa Japan) was mixed in an amount of 0.5 g as a lubricant with 100 g of a water-absorbent resin, to prepare a water-absorbent resin for measurement.

The above-mentioned water-absorbent resin was allowed to pass though a JIS standard sieve having a sieve opening of 250 μm, and a mass-average particle size was measured using a combination of sieves of (A) in a case where the resin was allowed to pass in an amount of 50% by mass or more, or a combination of sieves of (B) in a case where 50% by mass or more of the resin remained on the sieve.

(A) JIS standard sieves, a sieve having an opening of 425 μm, a sieve having an opening of 250 μm, a sieve having an opening of 180 μm, a sieve having an opening of 150 μm, a sieve having an opening of 106 μm, a sieve having an opening of 75 μm, a sieve having an opening of 45 μm, and a receiving tray were combined in order from the top.

(B) JIS standard sieves, a sieve having an opening of 850 μm, a sieve having an opening of 600 μm, a sieve having an opening of 500 μm, a sieve having an opening of 425 μm, a sieve having an opening of 300 μm, a sieve having an opening of 250 μm, a sieve having an opening of 150 μm, and a receiving tray were combined in order from the top.

The above-mentioned water-absorbent resin was placed on an uppermost sieve of the combined sieves, and shaken for 20 minutes with a rotating and tapping shaker machine to classify the resin.

After classification, the relationships between the opening of the sieve and an integral of a mass percentage of the water-absorbent resin remaining on the sieve were plotted on a logarithmic probability paper by calculating the mass of the water-absorbent resin remaining on each sieve as a mass percentage to an entire amount, and accumulating the mass percentages in order, starting from those having larger particle diameters. A particle diameter corresponding to a 50% by mass cumulative mass percentage is defined as a mass-average particle size by joining the plots on the probability paper in a straight line.

<Degree of Hydrophilicity of Fibrous Web>

In the present specification, the degree of hydrophilicity of the fibrous web was measured using an apparatus described in "Determination of Water Repellency" described in JAPAN TAPPI Test Method No. 68 (2000).

Specifically, a fibrous web test piece, which was cut into a rectangular strip having width×length dimensions of 10 cm×30 cm in a manner so that the longitudinal direction was a length direction (machine feeding direction) of the fibrous web, was attached to a test piece attaching apparatus sloped at 45°. A burette controlled at an opening of a cock of the burette so that 10 g of distilled water was supplied in 30 seconds was once dried, and fixed so that a part 5 mm above in a vertical direction from the uppermost part of a test piece attached to the sloped apparatus was arranged at the tip of the burette. About 60 g of distilled water was supplied from the upper part of the burette, and a time period (seconds) from the beginning of dripping of a liquid to a fibrous web test piece from the tip of the burette to a point where the liquid leaked out from a lower part because the test piece could not hold on to the liquid was measured, and defined as a degree of hydrophilicity of a fibrous web. It is judged that the larger the numerical values, the higher the degree of hydrophilicity.

Usually, the material itself of the fibrous web having hydrophilicity or a fibrous web provided with a hydrophilic treatment has a numerical value for a degree of hydrophilicity of 5 or more, while in a fibrous web of a material having a low hydrophilicity, liquids are more likely to run over near the surface and leak out from a lower part more quickly.

<Water-Retention Capacity of Saline Solution of Water-Absorbent Sheet Structure>

The water-absorbent sheet structure cut into a square having 7 cm each side was prepared as a sample, and the mass Wf (g) thereof was measured. The sample was placed in a cotton bag (Cottonbroad No. 60, width 100 mm×length 200 mm), and further the cotton bag was placed in a 500 mL-beaker. Saline solution was poured into the cotton bag in an amount of 500 g at one time, and the upper part of the cotton bag was then tied up with a rubber band, and the cotton bag was allowed to stand for 1 hour, to sufficiently make the sample swollen. The cotton bag was dehydrated for 1 minute with a dehydrator (manufactured by Kokusan Enshinki Co., Ltd., product number: H-122) set to have a centrifugal force of 167 G. The mass Wg (g) of the cotton bag containing sample after the dehydration was measured. The same procedures were carried out without adding the sample, and the empty mass Wh (g) of the cotton bag upon wetting was measured. The water-retention capacity of saline solution of the water-absorbent sheet structure was calculated from the following formula.

$$\text{Water-Retention Capacity of Saline Solution (g/m}^2\text{) of Water-Absorbent Sheet Structure} = [Wg - Wh - Wf] \text{ (g)} / 0.0049 \text{ (m}^2\text{)}$$

<Strength of Water-Absorbent Sheet Structure>

The strength of the water-absorbent sheet structure was evaluated in accordance with the following method.

Figure 3:
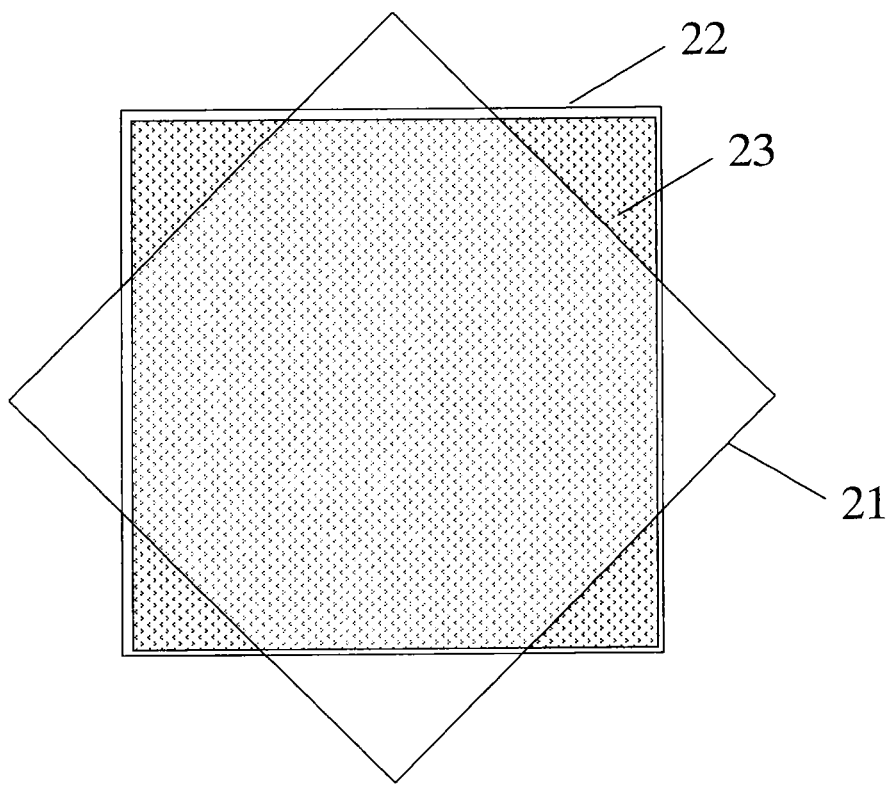
FIG. 3 A schematic view showing an outline of the constitution of an apparatus used for measuring strength for a water-absorbent sheet structure.

The resulting water-absorbent sheet structure was cut into a size of 10 cm×10 cm. Next, the entire side of each of one side of two pieces of acrylic plates of 10 cm×10 cm (mass: about 60 g) was adhered with a double-sided adhesive tape. As shown in FIG. 3, the above-mentioned sheet structure was adhered so as to overlay on an acrylic plate 22, in a manner that the diagonal lines of acrylic plates 21, 22 formed 45 degrees in angle, an acrylic plate 21 was adhered to a water-absorbent sheet structure 23 to fix with pressure so that the double-sided adhesive tape faced the side of the water-absorbent sheet structure 23.

The strength-test pieces of the water-absorbent sheet structure prepared in the manner as described above were placed on a metallic tray of sieves, used in the section of the above-mentioned <Mass-Average Particle Size of Water-Absorbent Resin>, and a lid was put thereon. Thereafter, the lidded metallic tray was tapped with rotations with a rotating and tapping shaker machine for 3 minutes. The strength of the water-absorbent sheet structure was evaluated based on the external appearance of the strength-test pieces after tapping in accordance with the following criteria.

◯: The water-absorbent sheet structure showed no changes in external appearance, and did not easily move even when the acrylic plates were tried to be displaced.

Δ: The water-absorbent sheet structure showed no changes in external appearance, but the water-absorbent sheet structure was split when the acrylic plates were displaced.

X: The water-absorbent sheet structure was split, and the contents were scattered.

<Feel of Water-Absorbent Sheet Structure>

The feel of a water-absorbent sheet structure was evaluated by the following method. A water-absorbent sheet structure obtained which was cut into a size of 10 cm×30 cm was used as a sample. Ten panelists were asked to make a three-rank evaluation on whether or not a sample satisfies both the softness and the shape-retention capacity of the water-absorbent sheet structure, in accordance with the following criteria, and the evaluation scores of the panelists were averaged to evaluate the feel of a water-absorbent sheet structure.

Rank A: The feel upon bending is soft, and the scattering of the contents are not observed (evaluation score: 5).

Rank B: There is a feel of resistance upon bending; the scattering of the contents are often observed, while feel is soft (evaluation score: 3).

Rank C: The sheet structure is less easily bendable, and has poorer recoverability after bending, or the sheet structure is too soft, so that scattering of the contents frequently takes place, and the fibrous web is easily turned over (evaluation score: 1).

<Peeling Strength (N/7 cm) of Water-Absorbent Sheet Structure>

The peeling strength of the water-absorbent sheet structure was measured in accordance with the following method. A water-absorbent sheet structure obtained was cut into a square having dimensions of 7 cm×7 cm. Next, one side of a test piece was evenly peeled for a part with a width of 2 cm in a manner that a length direction (machine feeding direction) of a fibrous web forming the water-absorbent sheet structure is to be a stretching direction.

The 2 cm width part that was peeled was fastened to each of upper and lower chucks of a tensile tester provided with chucks of a width of 8.5 cm (manufactured by Shimadzu Corporation, Autograph AGS-J), and the distance between the chucks were set to be at zero.

The test piece was stretched in a direction of 180° at a speed of 0.5 cm/minute, and test values (loads) were continuously recorded with a computer up to a distance between chucks of 4 cm. An average of the test values (loads) at a stretching distance of from 0 to 4 cm was defined as a peeling strength (N/7 cm) of a water-absorbent sheet structure. The measurements were taken 5 times, and a 3-point average excluding a minimum value and a maximum value was used.

<Measurement of Thickness of Water-Absorbent Sheet Structure>

A water-absorbent sheet structure, which was cut into rectangular strips having dimensions of 10 cm×30 cm in a manner that a longitudinal direction thereof is to be in a length direction (machine feeding direction) of the nonwoven fabric, was used as a sample. The thickness of the resulting water-absorbent sheet structure was measured using a thickness measurement instrument (manufactured by Kabushiki Kaisha Ozaki Seisakusho, model number: J-B) at three measurement sites taken in a longitudinal direction, on the left end, the center, and the right end; for example, the left end was set at a site 3 cm away from the left side, the center was set at a site 15 cm away therefrom, and the right end was set at a site 27 cm away therefrom. As the width direction, a central part was measured. The measurement value for thickness was obtained by measuring three times at each site, and an average for each site was obtained. Further, the values at the left end, the center, and the right end were averaged, which was defined as a thickness of an overall water-absorbent sheet structure.

<Evaluations of Total Permeation Rate and Amount of Re-Wet of Water-Absorbent Sheet Structure>

A water-absorbent sheet structure, which was cut into rectangular strips having dimensions of 10 cm×30 cm in a manner that a longitudinal direction thereof is to be in a length direction (machine feeding direction) of the fibrous web, was used as a sample.

In a 10 L container were placed 60 g of sodium chloride, 1.8 g of calcium chloride dihydrate, 3.6 g of magnesium chloride hexahydrate, and a proper amount of distilled water to completely dissolve. Next, 15 g of an aqueous 1% by mass poly(oxyethylene)isooctylphenyl ether solution was added thereto, and distilled water was further added to adjust the weight of the overall aqueous solution to 6000 g. Thereafter, the mixed solution was colored with a small amount of Blue No. 1 to prepare a test solution.

A polyethylene air-through style porous liquid-permeable sheet having the same size as the sample (10 cm×30 cm) and a basis weight of 22 g/m$^2$ was placed over an upper side of a sample (water-absorbent sheet structure). In addition, underneath the sample was placed a polyethylene liquid-impermeable sheet having the same size and basis weight as the sheet, to prepare a simple absorbent article. A cylindrical cylinder having an inner diameter of 3 cm was placed near the central section of this absorbent article, and a 50 mL test solution was supplied thereto at one time. At the same time, a time period until the test solution was completely permeated into the absorbent article was measured with a stopwatch, which is referred to as a first permeation rate (seconds). Next, the same procedures were carried out placing the cylindrical cylinder at the same position as the first permeation rate 30 minutes thereafter and 60 minutes thereafter, to measure second and third permeation rates (seconds). A total of the number of seconds for the first to third permeation rates is referred to as a total permeation rate.

After 120 minutes from the start of the feeding of the first test liquid, the cylinder was removed, filter papers (about 80 sheets) of 10 cm each side, of which mass (Wi (g), about 70 g) was previously measured, were stacked near the liquid supplying position of the absorbent article, and a 5 kg weight of which bottom side has dimensions of 10 cm×10 cm was placed thereon. After 5 minutes of applying a load, the mass (Wj (g)) of the filter papers was measured, and an increased mass was defined as the amount of re-wet (g) as follows.

$$\text{Amount of Re-wet}(g) = Wj - Wi$$

<Slope Leakage Test>

Figure 4:
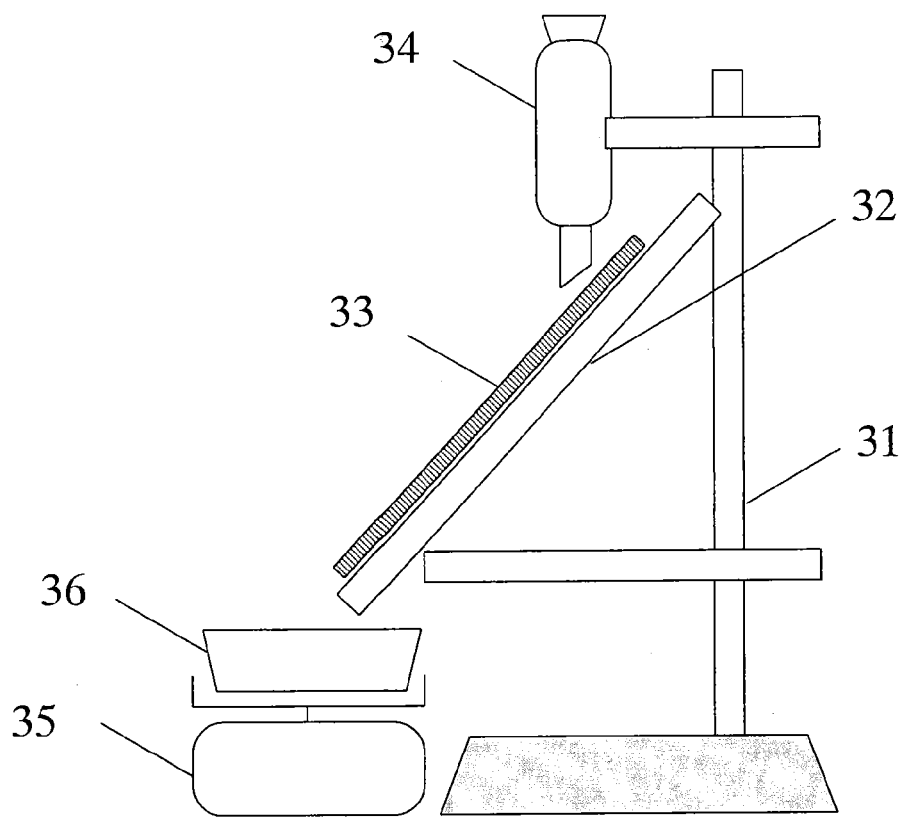
FIG. 4 A schematic view showing an outline of the constitution of an apparatus used for carrying out a slope leakage test for a water-absorbent sheet structure.

A slope leakage test was conducted using an apparatus shown in FIG. 4.

Schematically, a mechanism is as follows. A commercially available stand 31 for experimental facilities was used to slope an acrylic plate 32 and fixed, the above-mentioned test solution was then supplied to an absorbent article 33 placed on the plate from a dropping funnel 34 positioned vertically above the absorbent article, and a leakage amount was measured with a balance 35. The detailed specifications are given hereinbelow.

An acrylic plate 32 has a length in the direction of the slope plane of 45 cm, and fixed so that an angle formed with a stand 31 against the horizontal is 45°±2°. The acrylic plate 32 had a width of about 100 cm and a thickness of about 1 cm, and plural absorbent articles 33 could be concurrently measured. The acrylic plate 32 had a smooth surface, so that a liquid was not detained or absorbed to the plate.

A dropping funnel 34 was fixed at a position vertically above the sloped acrylic plate 32 using the stand 31. The dropping funnel 34 had a volume of 100 mL, and an inner diameter of a tip end portion of 4 mm, and an aperture of the cock was adjusted so that a liquid was supplied at a rate of 8 mL/s.

A balance 35 on which a metallic tray 36 was placed was set at a lower side of the acrylic plate 32, and all the test solutions flowing down the plate were received as leakage, and the mass was recorded to the accuracy of 0.1 g.

A slope leakage test using an apparatus as described above was carried out in accordance with the following procedures. The mass of a water-absorbent sheet structure cut into a rectangular strip having dimensions of width×length 10 cm×30 cm in a manner that the longitudinal direction is a length direction (machine feeding direction) of the fibrous web was measured, and an air through-style polyethylene liquid-permeable nonwoven fabric (basis weight: 22 g/m$^2$) of the same size was attached from an upper side thereof, and further a polyethylene liquid-impermeable sheet having the same basis weight of the same size was attached from a lower side thereof to prepare a simple absorbent article 33. The simple absorbent article 33 was adhered on the acrylic plate 32 (in order not to stop leakage intentionally, the bottom end of the absorbent article 33 was not adhered to the acrylic plate 32).

Marking was put on the absorbent article 33 at a position 2 cm away in a downward direction from a top end thereof, and a supplying inlet for the dropping funnel 34 was fixed so that the inlet was positioned at a distance 8 mm±2 mm vertically above the marking.

A balance 35 was turned on, and tared so that the indication was zero, and thereafter 80 mL of the above-mentioned test solution was supplied at one time to the dropping funnel 34. An amount of liquid poured into a metallic tray 36 after the test solution was allowed to flow over a sloped acrylic plate 32 without being absorbed into an absorbent article 33 was measured, and this amount of liquid was defined as a first leakage amount (g). The numerical value for this first leakage amount (g) was denoted as LW1.

Second and third test solutions were supplied in 10-minute intervals from the beginning of the first supply, and second and third leakage amounts (g) were measured, and the numerical values therefor were respectively denoted as LW2 and LW3.

Next, a leakage index was calculated in accordance with the following equation. The smaller the index, the smaller the leakage amount at a slope of a water-absorbent sheet structure, especially an initial leakage amount, whereby it is judged to be an excellent water-absorbent sheet structure.

Leakage Index: $L=LW1\times10+LW2\times5+LW3$

Production Example 1

Production of Water-Absorbent Resin A

A cylindrical round bottomed separable flask having an internal diameter of 100 mm, equipped with a reflux condenser, a dropping funnel, a nitrogen gas inlet tube, and a stirrer having two steps of a stirring blade having 4 inclined paddle blades with a blade diameter of 50 mm was furnished. This flask was charged with 500 mL of n-heptane, and 0.92 g of a sucrose stearate having an HLB of 3 (manufactured by Mitsubishi-Kagaku Foods Corporation, Ryoto sugar ester S-370) and 0.92 g of a maleic anhydride-modified ethylene-propylene copolymer (manufactured by Mitsui Chemicals, Inc., Hi-wax 1105A) were added thereto as surfactants. The temperature was raised to 80° C. to dissolve the surfactants, and thereafter the solution was cooled to 50° C.

On the other hand, a 500 mL-Erlenmeyer flask was charged with 92 g of an 80.5% by mass aqueous solution of acrylic acid, and 154.1 g of a 20.0% by mass aqueous sodium hydroxide was added dropwise thereto with cooling from external to neutralize 75% by mol. Thereafter, 0.11 g of potassium persulfate and 9.2 mg of N,N'-methylenebisacrylamide were added thereto to dissolve, to prepare an aqueous monomer solution for the first step.

An entire amount of the above-mentioned aqueous monomer solution was added to the above-mentioned separable flask, while setting a rotational speed of a stirrer to 450 r/min, and the temperature was kept at 35° C. for 30 minutes, while replacing the internal of the system with nitrogen. Thereafter, the flask was immersed in a water bath kept at 70° C., and a polymerization was carried out, to give a slurry after the first-step polymerization.

On the other hand, another 500 mL-Erlenmeyer flask was charged with 128.8 g of an 80.5% by mass aqueous solution of acrylic acid, and 174.9 g of a 24.7% by mass aqueous sodium hydroxide was added dropwise thereto with cooling from external to neutralize 75% by mol. Thereafter, 0.16 g of potassium persulfate and 12.9 mg of N,N'-methylenebisacrylamide were added thereto to dissolve, to prepare an aqueous monomer solution for the second step. The temperature was kept at about 25° C.

The agitation rotational speed of the stirrer containing the slurry after the polymerization mentioned above was changed to 1000 r/min, and the temperature was then cooled to 25° C. An entire amount of the aqueous monomer solution for the second step mentioned above was added to the internal of the system, and the temperature was held for 30 minutes while replacing the internal of the system with nitrogen. The flask was again immersed in a water bath at 70° C., and the temperature was raised to carry out polymerization, to give a slurry after the second-step polymerization.

Next, the temperature was raised using an oil bath at 120° C., and water and n-heptane were subjected to azeotropic distillation to remove 265.5 g of water to the external of the system, while refluxing n-heptane. Thereafter, 6.62 g of a 2% aqueous solution of ethylene glycol diglycidyl ether was added thereto, and the mixture was kept at 80° C. for 2 hours. Subsequently, n-heptane was evaporated to dryness, to give 232.1 g of a water-absorbent resin A in the form in which spherical particles are agglomerated. The resulting water-absorbent resin A had properties such as a mass-average particle size of 370 μm, a water-absorption rate of saline solution of 41 seconds, a water-retention capacity of saline solution of 35 g/g, a water-absorption capacity of saline solution under load of 4.14 kPa of 25 mL/g, an initial water-absorption rate of 0.18 mL/s and an effective amount of water absorbed of 57 mL/g.

Production Example 2

Production of Water-Absorbent Resin B

A cylindrical round bottomed separable flask having an internal diameter of 100 mm, equipped with a reflux condenser, a dropping funnel, a nitrogen gas inlet tube, and a stirrer having two steps of a stirring blade having 4 inclined paddle blades with a blade diameter of 50 mm was furnished. This flask was charged with 500 mL of n-heptane, and 0.92 g of a sucrose stearate having an HLB of 3 (manufactured by Mitsubishi-Kagaku Foods Corporation, Ryoto sugar ester S-370) and 0.92 g of a maleic anhydride-modified ethylene-propylene copolymer (manufactured by Mitsui Chemicals, Inc., Hi-wax 1105A) were added thereto as surfactants. The temperature was raised to 80° C. to dissolve the surfactants, and thereafter the solution was cooled to 50° C.

On the other hand, a 500 mL-Erlenmeyer flask was charged with 92 g of an 80.5% by mass aqueous solution of acrylic acid, and 154.1 g of a 20.0% by mass aqueous sodium hydroxide was added dropwise thereto with cooling from external to neutralize 75% by mol. Thereafter, 0.11 g of potassium persulfate and 9.2 mg of N,N'-methylenebisacrylamide were added thereto to dissolve, to prepare an aqueous monomer solution for the first step.

An entire amount of the above-mentioned aqueous monomer solution was added to the above-mentioned separable flask, while setting a rotational speed of a stirrer to 600 r/min, and the temperature was kept at 35° C. for 30 minutes, while replacing the internal of the system with nitrogen. Thereafter, the flask was immersed in a water bath kept at 70° C., and a polymerization was carried out, to give a slurry after the first-step polymerization.

On the other hand, another 500 mL-Erlenmeyer flask was charged with 128.8 g of an 80.5% by mass aqueous solution of acrylic acid, and 174.9 g of a 24.7% by mass aqueous sodium hydroxide was added dropwise thereto with cooling from external to neutralize 75% by mol. Thereafter, 0.16 g of potassium persulfate and 12.9 mg of N,N'-methylenebisacrylamide were added thereto to dissolve, to prepare an aqueous monomer solution for the second step. The temperature was kept at about 25° C.

The agitation rotational speed of the stirrer containing the slurry after the polymerization mentioned above was changed to 1000 r/min, and the temperature was then cooled to 28° C. An entire amount of the aqueous monomer solution for the second step mentioned above was added to the internal of the system, and the temperature was held for 30 minutes while replacing the internal of the system with nitrogen. The flask was again immersed in a water bath at 70° C., and the temperature was raised to carry out polymerization, to give a slurry after the second-step polymerization.

Next, the temperature was raised using an oil bath at 120° C., and water and n-heptane were subjected to azeotropic distillation to remove 269.8 g of water to the external of the system, while refluxing n-heptane. Thereafter, 8.83 g of a 2% aqueous solution of ethylene glycol diglycidyl ether was added thereto, and the mixture was kept at 80° C. for 2 hours. Subsequently, n-heptane was evaporated to dryness, to give 231.3 g of a water-absorbent resin B in the form in which spherical particles are agglomerated. The resulting water-absorbent resin B had properties such as a mass-average particle size of 300 μm, a water-absorption rate of saline solution of 24 seconds, a water-retention capacity of saline solution of 42 g/g, a water-absorption capacity of saline solution under load of 4.14 kPa of 18 mL/g, an initial water-absorption rate of 0.19 mL/s and an effective amount of water absorbed of 62 mL/g.

Production Example 3

Production of Water-Absorbent Resin C

The same procedures as in Production Example 2 of Water-Absorbent Resin B were carried out except that the amount of a 2% aqueous solution of ethylene glycol diglycidyl ether added after the removal of water to the external of the system by azeotropic distillation was changed to 16.56 g, in Production Example 2 mentioned above, to give 232.3 g of a water-absorbent resin C in the form in which the spherical particles were agglomerated. The resulting water-absorbent resin C had properties such as a mass-average particle size of 320 μm, a water-absorption rate of saline solution of 32 seconds, a water-retention capacity of saline solution of 23 g/g, a water-absorption capacity of saline solution under load of 4.14 kPa of 23 mL/g, an initial water-absorption rate of 0.15 mL/s and an effective amount of water absorbed of 42 mL/g.

Production Example 4

Production of Water-Absorbent Resin D

A cylindrical round bottomed separable flask having an internal diameter of 100 mm, equipped with a reflux condenser, a dropping funnel, a nitrogen gas inlet tube, and a stirrer having two steps of a stirring blade having 4 inclined paddle blades with a blade diameter of 50 mm was furnished. This flask was charged with 550 mL of n-heptane, and 0.84 g of a sorbitan monolaurate having an HLB of 8.6 (manufactured by manufactured by NOF Corporation, Nonion LP-20R) was added thereto as a surfactant. The temperature was raised to 50° C. to dissolve the surfactant, and thereafter the solution was cooled to 40° C.

On the other hand, a 500 mL-Erlenmeyer flask was charged with 70 g of an 80.5% by mass aqueous solution of acrylic acid, and 112.3 g of a 20.9% by mass aqueous sodium hydroxide was added dropwise thereto with cooling to neutralize 75% by mol. Thereafter, 0.084 g of potassium persulfate was added thereto to dissolve, to prepare an aqueous monomer solution.

An entire amount of the above-mentioned aqueous monomer solution was added to the above-mentioned separable flask, while setting a rotational speed of the stirrer to 800 r/min, and the internal of the system was replaced with nitrogen for 30 minutes. The flask was then immersed in a water bath at 70° C. to raise the temperature, and a polymerization reaction was carried out for two hours.

Next, the temperature was raised using an oil bath at 120° C., and water and n-heptane were subjected to azeotropic distillation to remove 85.5 g of water to the external of the system, while refluxing n-heptane. Thereafter, 8.5 g of a 2% aqueous solution of ethylene glycol diglycidyl ether was added thereto, and the mixture was kept at 80° C. for 2 hours. Subsequently, n-heptane was evaporated to dryness, to give 73.3 g of a water-absorbent resin D in a granular form. The resulting water-absorbent resin D had properties such as a mass-average particle size of 250 μm, a water-absorption rate of saline solution of 3 seconds, a water-retention capacity of saline solution of 24 g/g, a water-absorption capacity of saline solution under load of 4.14 kPa of 24 mL/g, an initial water-absorption rate of 0.34 mL/s and an effective amount of water absorbed of 42 mL/g.

Production Example 5

Production of Water-Absorbent Resin E

The same procedures as in Production Example 4 of Water-Absorbent Resin D were carried out except that the amount of a 2% aqueous solution of ethylene glycol diglycidyl ether added after the removal of water to the external of the system by azeotropic distillation was changed to 10.0 g, in Production Example 4 mentioned above, to give 72.5 g of a water-absorbent resin E in a granular form. The resulting water-absorbent resin E had properties such as a mass-average particle size of 220 μm, a water-absorption rate of saline solution of 3 seconds, a water-retention capacity of saline solution of 20 g/g, a water-absorption capacity of saline solution under load of 4.14 kPa of 23 mL/g, an initial water-absorption rate of 0.33 mL/s and an effective amount of water absorbed of 36 mL/g.

Production Example 6

Production of Water-Absorbent Resin F

The same procedures as in Production Example 4 of Water-Absorbent Resin D were carried out except that the amount of a 2% aqueous solution of ethylene glycol diglycidyl ether added after the removal of water to the external of the system by azeotropic distillation was changed to 3.50 g, in Production Example 4 mentioned above, to give 72.3 g of a water-absorbent resin F in a granular form. The resulting water-absorbent resin F had properties such as a mass-average particle size of 240 μm, a water-absorption rate of saline solution of 3 seconds, a water-retention capacity of saline solution of 38 g/g, a water-absorption capacity of saline solution under load of 4.14 kPa of 15 mL/g, an initial water-absorption rate of 0.34 mL/s and an effective amount of water absorbed of 63 mL/g.

Example 1

A roller spreader (manufactured by HASHIMA CO., LTD., SINTERACE M/C) was charged at its supplying inlet with a mixture prepared by homogeneously mixing 60 parts by mass of an ethylene-vinyl acetate copolymer (EVA; melting point: 95° C.) as an adhesive, 270 parts by mass of a water-absorbent resin A of Production Example 1 as a water-absorbent resin (A), and 65 parts by mass of a water-absorbent resin E of Production Example 5 as a water-absorbent resin (B) (a water-absorbent resin composition). On the other hand, a spunlace nonwoven fabric made of rayon having a width of 30 cm (basis weight: 40 g/m$^2$, thickness: 440 μm, rayon content: 100%, degree of hydrophilicity: 66, referred to as "Web A") as a fibrous web was spread over a conveyor at the bottom part of the spreader. Next, the spreading roller and the bottom part conveyor were operated, thereby allowing the above-mentioned mixture to evenly overlay the above-mentioned fibrous web at a basis weight of 395 g/m$^2$.

Figure 5:
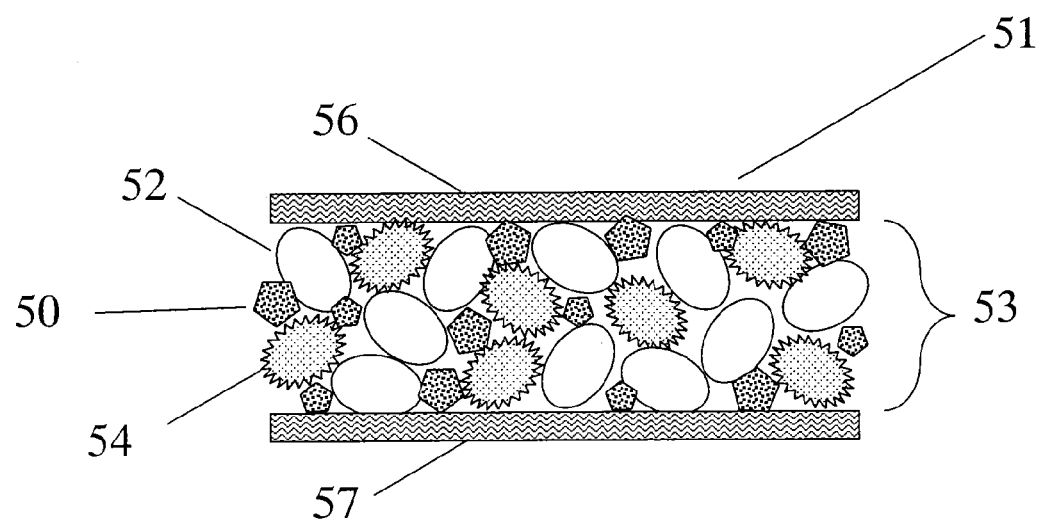
FIG. 5 A cross-sectional schematic view of one embodiment of a water-absorbent sheet structure according to the present invention.

The overlaid product obtained was sandwiched with another Web A, and thereafter heat-fused with a thermal laminating machine (manufactured by HASHIMA CO., LTD., straight linear fusing press HP-600LF) of which heating temperature was set at 130° C. to integrate, to give a water-absorbent sheet structure. The cross section of the resulting water-absorbent sheet structure, as schematically shown, had a structure as shown in FIG. 5. In FIG. 5, a water-absorbent sheet structure 51 had a structure in which an absorbent layer 53 is sandwiched with fibrous webs 56 and 57 from upper and lower sides of the absorbent layer 53. The absorbent layer 53 had a structure comprising a water absorbent resin (A) 52, a water absorbent resin (B) 54, and an adhesive 50. The resulting water-absorbent sheet structure was cut into a given size to perform the above-mentioned various measurements and evaluations. The results are shown in Table 2.

Example 2

A roller spreader (manufactured by HASHIMA CO., LTD., SINTERACE M/C) was charged at its supplying inlet with a mixture prepared by homogeneously mixing 100 parts by mass of low-density polyethylene (melting point: 107° C.) as an adhesive, 270 parts by mass of a water-absorbent resin A of Production Example 1 as a water-absorbent resin (A), and 65 parts by mass of a water-absorbent resin D of Production Example 4 as a water-absorbent resin (B) (a water-absorbent resin composition). On the other hand, spunlace nonwoven fabric made of rayon/polyethylene terephthalate having a width of 30 cm (basis weight: 35 g/m$^2$, thickness: 400 μm, rayon content: 70%, degree of hydrophilicity: 55, referred to as "Web B") as a fibrous web was spread over a conveyor at the bottom part of the spreader. Subsequently, the spreading roller and the bottom side conveyor were operated, thereby allowing the above-mentioned mixture to evenly overlay over the fibrous web at a basis weight of 435 g/m$^2$.

The overlaid product obtained was sandwiched with another Web B, and thereafter heat-fused with a thermal laminating machine (manufactured by HASHIMA CO., LTD., straight linear fusing press HP-600LF) of which heating temperature was set at 140° C. to integrate, to give a water-absorbent sheet structure. The water-absorbent sheet structure obtained was cut into a given size to perform the above-mentioned various measurements and evaluations. The results are shown in Table 2.

Example 3

The same procedures as in Example 2 were carried out except that in Example 2, the water-absorbent resin (B) used was changed to a water-absorbent resin C of Production Example 3, and that the content proportion of the adhesive was changed to those shown in Table 1 to give a water-absorbent sheet structure. The water-absorbent sheet structure obtained was cut into a given size to perform the above-mentioned various measurements and evaluations. The results are shown in Table 2.

Example 4

A SMS nonwoven fabric made of polypropylene having a width of 30 cm hydrophilically treated with a hydrophilic treatment agent (basis weight: 13 g/m$^2$, thickness: 150 polypropylene content: 100%, degree of hydrophilicity: 16, referred to as "Web C") as a fibrous web was spread over a hot melt applicator (manufactured by HALLYS Corporation, Marshall 150) of which heating temperature was set at 150° C., and thereafter a styrene-butadiene-styrene copolymer (SBS, softening point: 85° C.) was coated as an adhesive over the fibrous web at a basis weight of 20 g/m$^2$.

Next, a roller spreader (manufactured by HASHIMA CO., LTD., SINTERACE M/C) was charged at its supplying inlet with a mixture prepared by previously homogeneously mixing 200 parts by mass of the water-absorbent resin B as a water-absorbent resin (A) and 50 parts by mass of the water-absorbent resin E as a water-absorbent resin (B) (a water-absorbent resin composition). On the other hand, the above-mentioned web coated with an adhesive was spread over a conveyor at the bottom side of the spreader. Subsequently, the spreading roller and the bottom side conveyor were operated, thereby allowing the mixture of the water-absorbent resins to evenly overlay over the fibrous web at a basis weight of 250 g/m$^2$.

The overlaid product obtained was sandwiched from a top side with another fibrous web C to which the above-mentioned SBS was applied as an adhesive in the same manner as above at a basis weight of 20 g/m$^2$, and thereafter heat-fused with a thermal laminating machine (manufactured by HASHIMA CO., LTD., straight linear fusing press HP-600LF) of which heating temperature was set at 100° C. to integrate, to give a water-absorbent sheet structure. The results are shown in Table 2.

Example 5

The same procedures as in Example 4 were carried out except that in Example 4, the fibrous web used was changed to Web D listed in Table 3, that the water-absorbent resin (A) used was changed to a water-absorbent resin A of Production Example 1, and the contents of the water-absorbent resins and the adhesive and the like were changed as listed in Table 1 to give a water-absorbent sheet structure. The water-absorbent sheet structure obtained was cut into a given size to perform the above-mentioned various measurements and evaluations. The results are shown in Table 2.

Example 6

The same procedures as in Example 4 were carried out except that in Example 4, the contents of the water-absorbent resins and the adhesive and the like were changed as listed in Table 1 to give a water-absorbent sheet structure. The water-absorbent sheet structure obtained was cut into a given size to perform the above-mentioned various measurements and evaluations. The results are shown in Table 2.

Comparative Example 1

A roller spreader (manufactured by HASHIMA CO., LTD., SINTERACE M/C) was charged at its supplying inlet with a mixture prepared by homogeneously mixing 100 parts by mass of an ethylene-vinyl acetate copolymer (EVA; melting point: 95° C.) as an adhesive and 335 parts by mass of a water-absorbent resin A of Production Example 1 as a water-absorbent resin (A). On the other hand, a spunlace nonwoven fabric made of rayon having a width of 30 cm (basis weight: 40 g/m², thickness: 460 μm, rayon content: 100%, degree of hydrophilicity: 66, referred to as "Web A") as a fibrous web was spread over a conveyor at the bottom part of the spreader. Next, the spreading roller and the bottom part conveyor were operated, thereby allowing the above-mentioned mixture to evenly overlay the above-mentioned fibrous web at a basis weight of 435 g/m².

The overlaid product obtained was sandwiched with another Web A, and thereafter heat-fused with a thermal laminating machine (manufactured by HASHIMA CO., LTD., straight linear fusing press HP-600LF) of which heating temperature was set at 130° C. to integrate, to give a water-absorbent sheet structure. The resulting water-absorbent sheet structure was cut into a given size to perform the above-mentioned various measurements and evaluations. The results are shown in Table 2.

Comparative Example 2

The same procedures as in Comparative Example 1 were carried out except that in Comparative Example 1, the water-absorbent resin (A) used was changed to a water-absorbent resin E obtained in Production Example 5, and the contents of the water-absorbent resin and the adhesive and the like were changed as listed in Table 1 to give a water-absorbent sheet structure. The water-absorbent sheet structure obtained was cut into a given size to perform the above-mentioned various measurements and evaluations. The results are shown in Table 2.

Comparative Example 3

The same procedures as in Example 2 were carried out except that in Example 2, the water-absorbent resin (B) used was changed to a waterabsorbent resin F obtained in Production Example 6, to give a water-absorbent sheet structure. The water-absorbent sheet structure obtained was cut into a given size to perform the above-mentioned various measurements and evaluations. The results are shown in Table 2.

Comparative Examples 4 and 5

The same procedures as in Example 4 were carried out except that in Example 4, the content proportion of the adhesive used and the like was changed as listed in Table 1 to give each of water-absorbent sheet structures. The water-absorbent sheet structure obtained was cut into a given size to perform the above-mentioned various measurements and evaluations. The results are shown in Table 2.

TABLE 1

| Ex. No. | Fibrous Web Upper Side | g/m² | Lower Side | g/m² | Water-Absorbent Resin (A) Kinds | g/m² | Water-Retention Capacity | Water-Absorbent Resin (B) Kinds | g/m² | Water-Retention Capacity | Adhesive Kinds | g/m² | Content |
|---|---|---|---|---|---|---|---|---|---|---|---|---|---|
| Ex. 1 | Web A | 40 | Web A | 40 | Resin A | 270 | 35 | Resin E | 65 | 20 | EVA | 60 | 0.18 |
| Ex. 2 | Web B | 35 | Web B | 35 | Resin A | 270 | 35 | Resin D | 65 | 24 | Polyethylene | 100 | 0.30 |
| Ex. 3 | Web B | 35 | Web B | 35 | Resin A | 270 | 35 | Resin C | 65 | 23 | Polyethylene | 80 | 0.24 |
| Ex. 4 | Web C | 13 | Web C | 13 | Resin B | 200 | 42 | Resin E | 50 | 20 | SBS | 40 | 0.16 |
| Ex. 5 | Web D | 11 | Web D | 11 | Resin A | 350 | 35 | Resin E | 150 | 20 | SBS | 100 | 0.20 |
| Ex. 6 | Web E | 15 | Web E | 15 | Resin B | 150 | 42 | Resin D | 120 | 24 | SBS | 40 | 0.15 |
| Comp. Ex. 1 | Web A | 40 | Web A | 40 | Resin A | 335 | 35 | (none) | | | EVA | 60 | 0.18 |
| Comp. Ex. 2 | Web A | 40 | Web A | 40 | Resin E | 335 | 20 | (none) | | | EVA | 80 | 0.24 |
| Comp. Ex. 3 | Web B | 35 | Web B | 35 | Resin A | 270 | 35 | Resin F | 65 | 38 | Polyethylene | 100 | 0.30 |
| Comp. Ex. 4 | Web C | 13 | Web C | 13 | Resin B | 30 | 42 | Resin E | 10 | 20 | SBS | 40 | 1.00 |
| Comp. Ex. 5 | Web C | 13 | Web C | 13 | Resin B | 800 | 42 | Resin E | 250 | 20 | SBS | 100 | 0.10 |

The content proportion of the adhesive is a content (mass basis) of the adhesive based on the water-absorbent resin.

TABLE 2

| Ex. No. | Thickness (mm) | Permeation Rate (seconds) | | | | Amount of Re-wet (g) | Slope Leakage Test | | | | Peeling Strength N/7 cm | Water-Retention Capacity g/m² | Effective Water-Retaining Percentage | Strength | Feel |
|---|---|---|---|---|---|---|---|---|---|---|---|---|---|---|---|
| | | 1 | 2 | 3 | Total | | 1 | 2 | 3 | Index | | | | | |
| Ex. 1 | 1.1 | 33 | 21 | 28 | 82 | 5.9 | 3 | 0 | 0 | 30 | 1.09 | 7,740 | 72% | ○ | 4.9 |
| Ex. 2 | 1.0 | 33 | 25 | 31 | 89 | 7.2 | 4 | 0 | 0 | 40 | 1.42 | 7,260 | 66% | ○ | 4.8 |
| Ex. 3 | 0.8 | 35 | 26 | 31 | 92 | 4.7 | 5 | 0 | 0 | 50 | 1.28 | 7,500 | 69% | ○ | 4.8 |
| Ex. 4 | 1.0 | 33 | 25 | 30 | 88 | 4.8 | 4 | 0 | 0 | 40 | 1.07 | 7,140 | 76% | ○ | 4.7 |
| Ex. 5 | 1.2 | 30 | 21 | 25 | 76 | 3.4 | 1 | 0 | 0 | 10 | 1.22 | 10,060 | 66% | ○ | 4.6 |
| Ex. 6 | 1.0 | 35 | 26 | 36 | 97 | 6.3 | 5 | 0 | 0 | 50 | 1.11 | 6,610 | 72% | ○ | 4.7 |
| Comp. Ex. 1 | 1.3 | 44 | 30 | 38 | 112 | 1.3 | 25 | 0 | 0 | 250 | 1.14 | 8,210 | 70% | ○ | 4.8 |
| Comp. Ex. 2 | 1.1 | 40 | 32 | 29 | 101 | 23.0 | 1 | 10 | 10 | 70 | 0.98 | 5,290 | 79% | ○ | 4.7 |
| Comp. Ex. 3 | 1.1 | 48 | 35 | 41 | 124 | 9.2 | 14 | 6 | 10 | 180 | 1.39 | 7,750 | 65% | ○ | 4.7 |
| Comp. Ex. 4 | 0.5 | 48 | 36 | 42 | 126 | 32.0 | 29 | 0 | 0 | 290 | 2.87 | 580 | 40% | ○ | 2.7 |
| Comp. Ex. 5 | 2.3 | 35 | 31 | 37 | 103 | 8.3 | 13 | 5 | 0 | 155 | 0.08 | 35,500 | 92% *disintegrated | X | 2.3 |

TABLE 3

| Abbreviation | Structure | Material | Basis Weight g/m² | Thickness μm | Degree of Hydrophilicity |
|---|---|---|---|---|---|
| Nonwoven Fabric A | Spunlace | Rayon, PET | 40 | 440 | 66 |
| Nonwoven Fabric B | Spunlace | Rayon, PET | 35 | 400 | 55 |
| Nonwoven Fabric C | SMS | Polypropylene | 13 | 150 | 16 |
| Nonwoven Fabric D | SMS | Polypropylene | 11 | 120 | 12 |
| Nonwoven Fabric E | SMMS | Polypropylene | 15 | 170 | 20 |

It could be seen from the above results that the water-absorbent sheet structures of Examples had faster liquid permeation rates, smaller amounts of re-wet, smaller slope liquid leakages, and more favorable properties, as compared to those of Comparative Examples. More specifically, far more excellent liquid absorbent properties were obtained by mixing two kinds of water-absorbent resins in accordance with the description of the present invention than the cases where one kind of the water-absorbent resin was used in the same amount (Example 1 and Comparative Examples 1 and 2). In addition, it can be seen that even when the two kinds of the water-absorbent resins were mixed, if a difference in water-retention capacities therebetween did not satisfy the range as defined in the present invention, excellent liquid absorbent properties cannot be obtained (Example 2 and Comparative Example 3). It can be seen that excellent liquid absorbent properties cannot also be obtained in a case where the water-absorbent resins are contained in a total amount outside the range as defined in the present invention (Comparative Examples 4 and 5).

INDUSTRIAL APPLICABILITY

The water-absorbent sheet structure of the present invention can be used for absorbent articles in hygienic material fields, agricultural fields, construction material fields, and the like, among which the water-absorbent sheet structure can be suitably used for disposable diapers.

EXPLANATION OF NUMERICAL SYMBOLS

X measurement apparatus
1 burette section
2 lead tube
3 measuring platform
4 measuring section
5 water-absorbent resin
10 burette
11 air inlet tube
12 cock
13 cock
14 rubber plug
21 acrylic plate
22 acrylic plate
23 water-absorbent sheet structure
31 stand
32 acrylic plate
33 absorbent article
34 dropping funnel
35 balance
36 tray
40 cylinder
41 nylon mesh
42 weight
45 nonwoven fabric
50 adhesive
51 water-absorbent sheet structure
52 water-absorbent resin (A)
53 absorbent layer
54 water-absorbent resin (B)
56 fibrous web
57 fibrous web
65 stand
75 clamp

The invention claimed is:
1. A water-absorbent sheet structure comprising a structure in which an absorbent layer comprising a water-absorbent resin composition comprising a water-absorbent resin (A) and a water-absorbent resin (B) is sandwiched with fibrous webs from an upper side and a lower side of the absorbent layer, wherein the water-absorbent resin (A) and the water-absorbent resin (B) are contained in a total amount of from 100 to 1,000 g/m², and that the water-absorbent resin (A) and the water-absorbent resin (B) have the following properties:
  (1) the water-absorbent resin (A) having a water-retention capacity of saline solution (Ra) from 25 to 55 g/g;
  (2) the water-absorbent resin (B) having a water-retention capacity of saline solution (Rb) from 20 to 24 g/g; and
  (3) Ra and Rb satisfy the relationship: Ra−Rb≥5 (g/g)

wherein the water-absorbent resin (A) and the water-absorbent resin (B) are in a mass ratio, the water-absorbent resin (A): the water-absorbent resin (B), of from 90:10 to 80:20.

2. The water-absorbent sheet structure of claim 1, wherein the water-absorbent resin (B) has a water-absorption capacity of saline solution under load of 4.14 kPa of 15 mL/g or more.

3. The water-absorbent sheet structure of claim 1, wherein the fibrous webs are nonwoven fabrics comprising at least one fiber selected from the group consisting of rayon fibers, polyolefin fibers, and polyester fibers.

4. The water-absorbent sheet structure of claim 1, wherein the water-absorbent sheet structure satisfies properties (4) to (6):
  (4) a thickness of 5 mm or less, in a dry state;
  (5) a total permeation rate of 120 seconds or less; and
  (6) a leakage index of 150 or less.

5. An absorbent article, comprising:
  the water-absorbent sheet structure of claim 1, sandwiched between a liquid-permeable sheet and a liquid-impermeable sheet.

6. The water-absorbent sheet of claim 1, wherein the water-absorbent resin (A) and the water-absorbent resin (B) are contained in a total amount of from 150 to 800 g/m$^2$.

7. The water-absorbent sheet of claim 1, wherein the water-absorbent resin (A) and the water-absorbent resin (B) are contained in a total amount of from 200 to 700 g/m$^2$.

8. The water-absorbent sheet of claim 1, wherein the water-absorbent resin (A) and the water-absorbent resin (B) are contained in a total amount of from 220 to 600 g/m$^2$.

9. The water-absorbent sheet of claim 1, wherein the water-absorbent resin (A) has a water-retention capacity of saline solution (Ra) of from 20 to 55 g/g.

10. The water-absorbent sheet of claim 1, wherein the water-absorbent resin (A) has a water-retention capacity of saline solution (Ra) of from 25 to 55 g/g.

11. The water-absorbent sheet of claim 1, wherein the water-absorbent resin (A) has a water-retention capacity of saline solution (Ra) of from 30 to 50 g/g.

12. The water-absorbent sheet structure of claim 1, wherein the water-absorbent resin (B) has a water-absorption capacity of saline solution under load of 4.14 kPa of from 20 to 40 ml/g.

13. The water-absorbent sheet structure of claim 1, said the water-absorbent resin composition consists of a water-absorbent resin (A), a water-absorbent resin (B) and an adhesive.

* * * * *